United States Patent [19]
Yoshida et al.

[11] Patent Number: 5,948,883
[45] Date of Patent: Sep. 7, 1999

[54] HUMAN CRM1 PROTEIN

[75] Inventors: Minoru Yoshida, Kawaguchi; Sueharu Horinouchi, Tokyo; Kazunori Nishi, Ibaraki, all of Japan

[73] Assignee: Takeda Chemical Industries, Ltd., Ibaraki, Japan

[21] Appl. No.: 08/975,527

[22] Filed: Nov. 20, 1997

[30]     Foreign Application Priority Data

Nov. 29, 1996  [JP]  Japan ................................. 8-318949

[51] Int. Cl.⁶ .................................................. C07K 14/47
[52] U.S. Cl. .......................................... 530/300; 530/350
[58] Field of Search ..................................... 530/350, 300

[56]                  References Cited

PUBLICATIONS

Ngo et al, The Protein Folding Problem and Tertiary Structure Prediction, Mertz et al (eds.), Birkhauser, Boston, pp. 433 and 492–495, 1994.
Krontiris, Internal Medicine, 4th edition, Stein (ed.), pp. 699–715, 1994.
Caldwell, Yakubutsu Dotai (Xenobtioic Metabolism and Disposition), vol. 11(1): pp. 119–125, 1996.
Y. Adachi, et al., "Higher Order Chromosome Structure Is Affected by Cold–sensitive Mutations in a Schizosaccharomyces pombe Gene+ crml Which Encodes a 115–kD Protein Preferentially Localized in the Nucleus and at Its Periphery", The Journal of Cell Biology, 108: 1195–1207, Apr. 1989.
T. Toda, et al., "Fission Yeast pap1–Dependent Transcription Is Negatively Regulated by an Essential Nuclear Protein, crm1", Molecular and Cellular Biology, 5474–5484, Dec., 1992.
P. Angel, et al., "The role of Jun, Fos and the AP–1 complex in cell–proliferation and transformation", Biochimica et Biophysica Acta., 1072:129–157 (1991).
K. Nishi, et al., "Leptomycin B Targets a Regulatory Cascade of crm1, a Fission Yeast Nuclear Protein, Involved in Control of Higher Order Chromosome Structure and Gene Expression", The Journal of Biological Chemistry, 269(9):6320–6324 (1994).
M. Fornerod, et al., "The human homologue of yeast CRML1 is in a dynamic subcomplex with CAN/NUP214 and a novel nuclear pore componenet Nup88", The EMBO Journal, 16(4):807–816 (1997).
B. Wolff, et al., "Leptomycin B is an inhibitor of nuclear export: inhibition of nucleo–cytoplasmic translocation of the human immunodeficiency virus type 1 (HIV–1) Rev protein and Rev–dependent mRNA", Chemistry & Biology, 4:139–147, Feb. 1997.
K. Ullman, et al., "Nuclear Export Receptors: From Imporitn to Exportin", Cell, 90:967–970, Sep. 1997.
K. Stade, et al. "Exportin 1 (Crm1p) Is an Essential Nuclear Export Factor", Cell, 90:1041–1050, Sep. 1997.
M. Fornerod, et al., "CRM1 Is an Export Receptor for Leucine–Rich Nuclear Export Signals", Cell, 90:1051–1060, Sep. 1997.
B. Ossareh–Nazari, et al. "Evidence for a Role of CRM1 in a Signal–Mediated Nuclear Protein Export", Science, 278:141–144, Oct. 1997.
M. Fukuda, et al., "CRM1 is responsible for intracellular transport mediated by the nuclear export sgnal signal", Nature, 390:308–311, Nov. 1997.
M. Neville, et al., "The importin–beta family member Crm1p bridges the interaction between Rev and the nuclear pore complex during nuclear export", Current Biology 7:767–775, (1997).
N. Kudo, et al., "Analysis of human CRM1 protein and its inhibitor Leptomycin B", Abstract of The Japanese Biochemical Society, Biochemistry (69(7):849, (1997) (in Japanese with partial English translation of pertinent part).
M. Yoshida, et al., "Function of human Crm1 protein as a target of Leptomycin anti–tumor substance and cell cycle signal transfer", Abstract of presentation at meeting of a Study Group of Molecular Target Therapy, p. 26, W–15 held on Jun. 6–7, 1997 (in Japanese with English translation of pertinent part).
N. Kudo, et al., "Cloning and characterization of the human homologue of yeast Crm1 protein", Abstract of presentation at 2nd "Sentan Gan" Younger Researcher Conference, "Control of Cell Proliferation", p. 267, Jan. 15–18, (1997).
E. Nishida, et al., "Leptomycin B Inhibition of NES–dependent Nuclear Export by Direct Binding to CRM1", The 3rd UK–Japan Cell Cycle Workshop, p. 23, Nov. 24–27, 1997.
M. Yoshida, et al., "Molecular Biology of the Cellular Targets of Cell Cycle Inhibitors that affect Nuclear Functions", The Sixteenth International Symposium on the Life Sciences, p. 38–41, Oct. 6–9, 1997.
Abstract of presentation at Japan Society to Bioscience, Biotechnology and Arochemistry, Nippon Nogeikagaku Kaishi,p. 17 Mar., 17, 1997 (in Japanese with English translation of pertinent part).
N. Kudo, et al. "Molecular Cloning and Cell Cycle–dependent Expression of Mammolian CRM1, a Protein Involved in Nuclear Export of Proteins", The Journal of Biology Chemistry, 272(47):29742–29751, (1997).

*Primary Examiner*—Terry McKelvey
*Attorney, Agent, or Firm*—William T. Han; Ratner & Prestia; William T. King

[57]                  ABSTRACT

A protein which comprises the sane or substantially the same amino acid sequence as that represented by SEQ ID NO:1, its partial peptide and their salts are disclosed. DNA encoding the protein or its partial peptide is also disclosed. The protein, its partial peptide or a salt thereof is an inhibitory factor of a transcription factor and, therefore, it is useful as medicine such as prophylactic and therapeutic drugs of, for example, tumors. The DNA is useful as a gene diagnosing drug. The antibody against the protein, etc. is also disclosed. The antibody is used for, for example, quantitative determination of the protein, etc. in a specimen fluid. The protein, etc. are also useful as a reagent for screening for compounds or their salts which promote the function of the protein, etc.

7 Claims, 7 Drawing Sheets

```
TTCAATCTCTGGTAATCTATGCCAGCAATTATGACAATTGTTAGCAGACCATGCAGCTCGTCAGCTGCTTGATTTC   75
                    MetProAlaIleMetThrMetLeuAlaAspHisAlaAlaArgGlnLeuLeuAspPhe

AGCCAAAAACTGGATATCAACTTATTAGATAATGTGGTGAATGCTTATACCATGGAGAAGGAGCCCAGCAAAGA     150
SerGlnLysLeuAspIleAsnLeuLeuAspAsnValAsnCysLeuTyrHisGlyGluGlyAlaGlnGlnArg

ATGGCTCAAGAAGTACTGACACATTTAAAGGAGCATCCTGATGCTTGGACAAGAGTCGACACAATTTTGGAATTT   225
MetAlaGlnGluValLeuThrHisLeuLysGluHisProAspAlaTrpThrArgValAspThrIleLeuGluPhe

TCTCAGAATATGAATACGAAATACTATGGACTACAAATTTTGGAAAATGTGATAAAAACAAGGTGGAACATTCTT   300
SerGlnAsnMetAsnThrLysTyrTyrGlyLeuGlnIleLeuGluAsnValIleLysThrArgTrpLysIleLeu

CCAAGGAACCAGTGCGAAGGAATAAAAAAAATACGTTGTTGGCCTCATTATCAAGACGTCATCTGACCAACTTGT   375
ProArgAsnGlnCysGluGlyIleLysLysTyrValValGlyLeuIleIleLysThrSerSerAspProThrCys

GTAGAGAGAAAAGGTGTATATCGGAAAATTAAATATGATCCTTGTTCAGATACTGAAACAAGAATGGCCCAAA    450
ValGluLysValTyrIleGlyLysLeuAsnMetIleLeuLeuValGlnIleLeuLysGlnGluTrpProLys

CATTGGCCAACTTTATCAGTGATATTGTTGGAGCAAGTAGGACCAAGCCGAAAGTCTCTGTCAAATATATGGTG   525
HisTrpProThrPheIleSerAspIleValGlyAlaSerArgThrSerGluSerLeuCysGlnAsnAsnMetVal

ATTCTTAAACTCTTGAGTGAAGAGTATTTGATTTCTCTAGTGGACAGATAACCAAGTCAAATCTAAGCATTTA   600
IleLeuLysLeuLeuSerGluGluTyrLeuIleSerLeuValAspArgEnd(?)

AAAGACAGCATGTCAATGAATTCTCACAGATATTTCAACTGTTCAGTTTGTAATGAAAATTCTCAAAATGCT    675
LysAspSerMetCysAsnGluPheSerGlnIleIlePheGlnLeuCysGlnPheValMetGluAsnSerGlnAsnAla
```

FIG. 1A

```
CCACTTGTACATGCAACCTTGGAAACATTGCTCAGATTTCTGAACTGGATTCCCCTGGGATATATTTTTGAGACC   750
ProLeuValHisAlaThrLeuGluThrLeuGluLeuArgPheLeuAsnTrpIlePheLeuGlyTyrIlePheGluThr

AAATTAATCAGCACATTGATTATAAGTTCCTGAAATGTTCCAATGTTTCGAAATGTCTCTGAAGTGCCTCACT   825
LysLeuIleSerThrLeuIleIleSerSerGluMetPheGlnCysSerAsnValSerLeuLeuLysCysLeuThr

GAGATTGCTGGTGTGAGTGTAAGCCAATATGAAGAACAATTGTAACACTATTACTCTGACAATGATGCAACTA   900
GluIleAlaGlyValSerValSerGlnTyrGluGluGlnPheValThrLeuPheThrLeuThrMetMetGlnLeu

AAGCAGATGCTTCCTTAAATACCAATATTCGACTTGCGTACTCAAATGGAAAGATGAACAGAACTTCATT   975
LysGlnMetLeuProLeuAsnThrAsnIleArgLeuAlaTyrSerAsnGlyLysAspGluGlnAsnPheIle

CAAAATCTCAGTTTGTTTCTCTGCACCTTTCTTAAGGAACATGATCAACTTATAGAAAAAGATTAAATCTCAGG   1050
GlnAsnLeuSerLeuPheLeuCysThrPheLeuLysGluHisAspGlnLeuIleGluLysArgLeuAsnLeuArg

GAAACTCTTATGGAGGCCCTTCATTATATGTTGTTGGTATCTGAAGTAGAAGAAACTGAAATCTTTAAAATTGT   1125
GluThrLeuMetGluAlaLeuHisTyrMetLeuLeuValSerGluValGluGluThrGluIlePheLysIleCys

CTTGAATACTGGAATCATTGGCTGCTGAACTCTATAGAGAGAGTCCATTCTCTACATCTGCCTCTCCGTTGCTT   1200
LeuGluTyrTrpAsnHisLeuAlaAlaGluLeuTyrArgGluSerProPheSerThrSerAlaSerProLeuLeu

TCTGAAGTCAACATTTGATGTTCCTCCCAGGAGACAGCTATATTGCCCATGTTATTCAAGGTCCGTTATTA   1275
SerGlySerGlnHisPheAspValProProArgArgGlnLeuTyrLeuProMetLeuPheLysValArgLeuLeu
```

FIG. 1B

```
ATGGTTAGTCGAATGGCTAAACCAGAGGAAGTATTGGTTGTAGAGAATGATCAAGGAGAAGTTGTGAGAGAATTC  1350
MetValSerArgMetAlaLysProGluGluValLeuValValGluAsnAspGlnGlyGluValValArgGluPhe

ATGAAGGATACAGATTCCATAAATTTGTATAAGAATATGAGGGAAACATTGGTTACTTTACTCTTCATCTGATTAT  1425
MetLysAspThrAspSerIleAsnLeuTyrLysAsnMetArgGluThrLeuValThrLeuTyrLeuThrHisLeuAspTyr

GTAGATACAGAAAGAATAATGACAGAGAAGCTTCACAATCAAGTGAATGGTACAGAGTGGTCATGGAAAAATTTG  1500
ValAspThrGluArgIleMetThrGluLysLeuHisAsnGlnValAsnGlyThrGluTrpSerTrpLysAsnLeu

AATACATTGTGTTGGGCAATAGGCTCCATTAGTGGAGCAATGCATGAAGAGGACGAAAAACGATTTCTTGTTACT  1575
AsnThrLeuCysTrpAlaIleGlySerIleSerGlyAlaMetHisGluGluAspGluLysArgPheLeuValThr

GTTATATAAAGGATCTATTAGGATTATGTGAACAGAAAGAGGCAAAGATAATAAAGCTATTATTGCATCAAATATC  1650
ValIleLysAspLeuLeuGlyLeuCysGluGlnLysGluGlnLysArgGlyLysAspAsnLysAlaIleIleAlaSerAsnIle

ATGTACATAGTAGGTCAATACCCACGTTTTTGAGAGCTCACTGGAAATTTCTGAAGACTGTAGTTGTAAACAAGCTG  1725
MetTyrIleValGlyGlnTyrProArgPheLeuArgAlaHisTrpLysPheLeuLysThrValValAsnLysLeu

TTCGAATTCATGCATGAGACCCATGAGTCCAGGATATGGCTTGTGATACTTTCATTAAAATAGCCCAAAAA  1800
PheGluPheMetHisGluThrHisGluSerArgIleTrpLeuValIleLeuSerLeuLysIleAlaGlnLys

TGCCGCAGGCATTTCGTTCAGTTGGAGAAGTGATGCCATTATTGATGAAATTTGAACAACATTAAC  1875
CysArgArgHisPheValGlnValGlyGluValMetProPheIleAspGluIleLeuAsnAsnIleAsn
```

FIG. 1C

```
ACTATTATTGTGATCTTCAGCCTCAACAGGTTCATACGTTTATGAAGCTGTGGGTACATGATTGGTGCACAA  1950
ThrIleIleCysAspLeuGlnProGlnValHisThrPheTyrGluAlaValGlyTyrMetIleGlyAlaGln

ACAGATCAAACACTACAAGAACACTTGATAGAAAAGTACATGTTACTCCCTAATCAAGTGTGGATAGTATAATC  2025
ThrAspGlnThrValGlnHisLeuIleGluLysTyrMetLeuLeuProAsnGlnValTrpAspSerIleIle

CAGCAGGCAACCAAAAATGTGGATATACTGAAAGATCCTGAAACAGTCAAGCAGCTTGGTAGCATTTGAAAACA  2100
GlnGlnAlaThrLysAsnValAspIleLeuLysAspProGluThrValLysGlnLeuGlySerIleLeuLysThr

AATGTGAGAGCCTGCAAAGCTGTTGGACACCCCTTTGTAATTCAGCTTGGAAGAATTTATTAGATATCCTTAAT  2175
AsnValArgAlaCysLysAlaValGlyHisProPheValIleGlnLeuGluGluPheIleLeuAspIleLeuAsn

GTATACAAGTGCCTCAGTGAAAATATTTCTCCAGCTATCCAAGCTAATGGTGAAATGGTTACAAAGCAACCATTG  2250
ValTyrLysCysLeuSerGluAsnIleSerAlaAlaIleGlnAlaAsnGlyGluMetValThrLysGlnProLeu

ATTAGAAGTATGCGAACTGTAAAAAGGGAAACTTTAAAGTTAATATCTGGTTGGGTGAGCCGATCCAATGATCCA  2325
IleArgSerMetArgThrValLysArgGluThrLeuLysLeuIleSerGlyTrpValSerArgSerAsnAspPro

CGATGGTCGCTGAAAATTTGTTCCCCCTCTGTTGATGCAGTTCTCATTGATTATCAGAGAAATGTCCCAGCT  2400
GlnMetValAlaGluAsnPheValProProLeuLeuAspAlaValLeuIleAspTyrGlnArgAsnValProAla

GCTAGAGAACCAGAAGTGCTTAGTACTATGGCCATAATTGTCAACAAGTTAGGGGACATATAACAGCTGAAATA  2475
AlaArgGluProGluValLeuSerThrMetAlaIleIleValAsnLysLeuGlyHisIleThrAlaGluIle
```

FIG. 1D

```
CCTCAAATATTTGATGCTGTGTTTTTGAATGCACATTGAATATGATAAATAAGGACTTTGAAGAATATCCTGAACAT  2550
ProGlnIlePheAspAlaValPheGluCysThrLeuAsnMetIleAsnLysAspPheGluGluTyrProGluHis

AGAACGAACTTTTTCTTACTACTTCAGGCTGTCAATTCCATTCCCAGCATTCCTGTTTCCTGCTATTCCACCTACA  2625
ArgThrAsnPhePheLeuLeuLeuLeuGlnAlaValAlaAsnSerHisCysPheProAlaPheLeuAlaIleProProThr

CAGTTTAAACTTGTTTGGATTCCATCATTTGGGCTTTCAAACATACTATGAGGAATGTCGCAGATACGGGCTTA  2700
GlnPheLysLeuValLeuAspSerIleIleTrpAlaPheLysHisThrMetArgAsnValAlaAspThrGlyLeu

CAGATACTTTTACACTCTTACAAAATGTTGCACAAGAAGCTGCAGAGTTTTATCAAACTTATTTT  2775
GlnIleLeuPheThrLeuLeuGlnAsnValAlaGlnGluAlaAlaAlaGlnSerPheTyrGlnThrTyrPhe

TGTGATATTCCAGCATATCTTTCTGTTGTGACAGACACTTCACATACTGCTGTTTAACAATGCATGCATCA  2850
CysAspIleLeuGlnHisIlePheSerValValThrAspThrSerHisThrAlaGlyLeuThrMetHisAlaSer

ATTCTTGCATATATGTTTAATTGGTTGAAGAAGAAGGAAAAATAAGTACATCATTAAATCCTGGAAATCCAGTTAAC  2925
IleLeuAlaTyrMetPheAsnLeuValGluGluGluGlyLysIleSerThrSerLeuAsnProGlyAsnProValAsn

AACCAAATCTTTCTTCAGGAATATGTCCCTAAGTCGGCCTTCCCTCACCTACAAGATGCTCAAGTA  3000
AsnGlnIlePheLeuGlnGluTyrValAlaAsnLeuLeuLysSerAlaPheProHisLeuGlnAspAlaGlnVal

AAGCTCTTTGTGACAGGGCTTTCAGCTTAAATCAAGATATTCCTGCTTTCAAGGAACATTAAGAGATTCCTA  3075
LysLeuPheValThrGlyLeuPheSerLeuAsnGlnAspIleProAlaPheLysGluHisLeuArgAspPheLeu
```

FIG. 1E

```
GTTCAAATAAAGGAATTTGCAGGTGAAGACACTTCTGATTTGTTTTTGGAAGAGAGAGAGAAATAGCCCTACGGCAG  3150
 ValGlnIleLysGluPheAlaGlyGluAspThrSerAspLeuPheLeuGluGluArgGluIleAlaLeuArgGln

GCTGATGAAGAGAAAACATAAACGTCAAATGTCTGTCCCTGGCATCTTTAATCCACATGAGATTCCAGAAGAAATG  3225
 AlaAspGluGluLysHisLysArgGlnMetSerValProGlyIlePheAsnProHisGluIleProGluGluMet

TGTGATTAAAATCCAAATTCATGCTGTTTTTTTCTCTGCAACTCGTTAGCAGAGGAAAACAGCATGTGGATTT     3300
 CysAsp*

TGTCGGCCAAAATGATGCCAATTTGTAAATTAAAATGTCACCTAGTGGCCCTTTTCTTATGTGTTTTTTGTAT    3375

AAGAAATTTCTGTGAAATATCCTTCCATTGTTTAAGCTTTTGTCATCTTTATTAGTTGCATGAAGT           3450

TGAAAATTAAGCCATTTTTAAAAATTTACTTCATGCCCATTTTGTGGCTGGGCTGGGGGAGGAGGCAAATTC     3525

GATTTGAACATATACTTGTAATTCTAATGCAAAATTATACAATTTTCCTGTAAACAATACCAATTTTAATTAG    3600

GGAGCATTTCCTTCTAGTCTATTCAGCCTAGAAGAAAAGATAATGAGTAAAACAAATTGCGTTGTTAAAGGA     3675

TTATAGTGCTGCATTGTCTGAAGTTAGCACCTCTTGGACTGTTGTCTAGACTACATGTATTACAAAGTC        3750

TCTTTGGCAAGATTGCAGCAAGATCATGTGCATATCATCCCATTGTAAAGCGACTTCAAAAATATGGAACACAG   3825

TTAGTTATTTTACACAGTTCTTTTTTGTTTTTGTGTGTTGCGTCGCTTGTCGACAACAGCTTTTTGTTTTC      3900

CTCAATGAGGAGTGTTGCTCATTTGTGAGCCTTCATTAACTCGAAGTGAAATGGTTAAAAATATTATCCGTTA    3975

GAATAGGCTGCATCTTTTAACAACTCATTAAAAAACAAAACAACTCGGCTTTTGAGATGACTTATACTAATT     4050
```

FIG. 1F

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 1071 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:1:

```
Met Pro Ala Ile Met Thr Met Leu Ala Asp His Ala Ala Arg Gln Leu
 1               5                  10                  15

Leu Asp Phe Ser Gln Lys Leu Asp Ile Asn Leu Leu Asp Asn Val Val
            20                  25                  30

Asn Cys Leu Tyr His Gly Glu Gly Ala Gln Gln Arg Met Ala Gln Glu
        35                  40                  45

Val Leu Thr His Leu Lys Glu His Pro Asp Ala Trp Thr Arg Val Asp
    50                  55                  60

Thr Ile Leu Glu Phe Ser Gln Asn Met Asn Thr Lys Tyr Tyr Gly Leu
65                  70                  75                  80

Gln Ile Leu Glu Asn Val Ile Lys Thr Arg Trp Lys Ile Leu Pro Arg
                85                  90                  95

Asn Gln Cys Glu Gly Ile Lys Lys Tyr Val Val Gly Leu Ile Ile Lys
            100                 105                 110

Thr Ser Ser Asp Pro Thr Cys Val Glu Lys Glu Lys Val Tyr Ile Gly
        115                 120                 125

Lys Leu Asn Met Ile Leu Val Gln Ile Leu Lys Gln Glu Trp Pro Lys
    130                 135                 140

His Trp Pro Thr Phe Ile Ser Asp Ile Val Gly Ala Ser Arg Thr Ser
145                 150                 155                 160

Glu Ser Leu Cys Gln Asn Asn Met Val Ile Leu Lys Leu Leu Ser Glu
                165                 170                 175

Glu Val Phe Asp Phe Ser Ser Gly Gln Ile Thr Gln Val Lys Ser Lys
            180                 185                 190

His Leu Lys Asp Ser Met Cys Asn Glu Phe Ser Gln Ile Phe Gln Leu
        195                 200                 205

Cys Gln Phe Val Met Glu Asn Ser Gln Asn Ala Pro Leu Val His Ala
    210                 215                 220

Thr Leu Glu Thr Leu Leu Arg Phe Leu Asn Trp Ile Pro Leu Gly Tyr
225                 230                 235                 240

Ile Phe Glu Thr Lys Leu Ile Ser Thr Leu Ile Tyr Lys Phe Leu Asn
                245                 250                 255

Val Pro Met Phe Arg Asn Val Ser Leu Lys Cys Leu Thr Glu Ile Ala
            260                 265                 270

Gly Val Ser Val Ser Gln Tyr Glu Glu Gln Phe Val Thr Leu Phe Thr
        275                 280                 285

Leu Thr Met Met Gln Leu Lys Gln Met Leu Pro Leu Asn Thr Asn Ile
    290                 295                 300

Arg Leu Ala Tyr Ser Asn Gly Lys Asp Asp Glu Gln Asn Phe Ile Gln
305                 310                 315                 320
```

```
Asn Leu Ser Leu Phe Leu Cys Thr Phe Leu Lys Glu His Asp Gln Leu
            325                 330                 335
Ile Glu Lys Arg Leu Asn Leu Arg Glu Thr Leu Met Glu Ala Leu His
        340                 345                 350
Tyr Met Leu Leu Val Ser Glu Val Glu Thr Glu Ile Phe Lys Ile
        355                 360                 365
Cys Leu Glu Tyr Trp Asn His Leu Ala Ala Glu Leu Tyr Arg Glu Ser
            370                 375                 380
Pro Phe Ser Thr Ser Ala Ser Pro Leu Leu Ser Gly Ser Gln His Phe
385                 390                 395                 400
Asp Val Pro Pro Arg Arg Gln Leu Tyr Leu Pro Met Leu Phe Lys Val
                405                 410                 415
Arg Leu Leu Met Val Ser Arg Met Ala Lys Pro Glu Val Leu Val
            420                 425                 430
Val Glu Asn Asp Gln Gly Glu Val Val Arg Glu Phe Met Lys Asp Thr
            435                 440                 445
Asp Ser Ile Asn Leu Tyr Lys Asn Met Arg Glu Thr Leu Val Tyr Leu
450                 455                 460
Thr His Leu Asp Tyr Val Asp Thr Glu Arg Ile Met Thr Glu Lys Leu
465                 470                 475                 480
His Asn Gln Val Asn Gly Thr Glu Trp Ser Trp Lys Asn Leu Asn Thr
                485                 490                 495
Leu Cys Trp Ala Ile Gly Ser Ile Ser Gly Ala Met His Glu Glu Asp
            500                 505                 510
Glu Lys Arg Phe Leu Val Thr Val Ile Lys Asp Leu Leu Gly Leu Cys
        515                 520                 525
Glu Gln Lys Arg Gly Lys Asp Asn Lys Ala Ile Ile Ala Ser Asn Ile
    530                 535                 540
Met Tyr Ile Val Gly Gln Tyr Pro Arg Phe Leu Arg Ala His Trp Lys
545                 550                 555                 560
Phe Leu Lys Thr Val Val Asn Lys Leu Phe Glu Phe Met His Glu Thr
                565                 570                 575
His Asp Gly Val Gln Asp Met Ala Cys Asp Thr Phe Ile Lys Ile Ala
            580                 585                 590
Gln Lys Cys Arg Arg His Phe Val Gln Val Gln Val Gly Glu Val Met
        595                 600                 605
Pro Phe Ile Asp Glu Ile Leu Asn Asn Ile Asn Thr Ile Ile Cys Asp
    610                 615                 620
Leu Gln Pro Gln Gln Val His Thr Phe Tyr Glu Ala Val Gly Tyr Met
625                 630                 635                 640
Ile Gly Ala Gln Thr Asp Gln Thr Val Gln Glu His Leu Ile Glu Lys
                645                 650                 655
Tyr Met Leu Leu Pro Asn Gln Val Trp Asp Ser Ile Ile Gln Gln Ala
            660                 665                 670
Thr Lys Asn Val Asp Ile Leu Lys Asp Pro Glu Thr Val Lys Gln Leu
        675                 680                 685
Gly Ser Ile Leu Lys Thr Asn Val Arg Ala Cys Lys Ala Val Gly His
    690                 695                 700
Pro Phe Val Ile Gln Leu Gly Arg Ile Tyr Leu Asp Met Leu Asn Val
705                 710                 715                 720
Tyr Lys Cys Leu Ser Glu Asn Ile Ser Ala Ala Ile Gln Ala Asn Gly
                725                 730                 735
Glu Met Val Thr Lys Gln Pro Leu Ile Arg Ser Met Arg Thr Val Lys
            740                 745                 750
```

```
Arg Glu Thr Leu Lys Leu Ile Ser Gly Trp Val Ser Arg Ser Asn Asp
        755                 760                 765
Pro Gln Met Val Ala Glu Asn Phe Val Pro Leu Leu Asp Ala Val
        770                 775                 780
Leu Ile Asp Tyr Gln Arg Asn Val Pro Ala Ala Arg Pro Glu Val
785                 790                 795                 800
Leu Ser Thr Met Ala Ile Ile Val Asn Lys Leu Gly His Ile Thr
                805                 810                 815
Ala Glu Ile Pro Gln Ile Phe Asp Ala Val Phe Glu Cys Thr Leu Asn
        820                 825                 830
Met Ile Asn Lys Asp Phe Glu Glu Tyr Pro Glu His Arg Thr Asn Phe
        835                 840                 845
Phe Leu Leu Leu Gln Ala Val Asn Ser His Cys Phe Pro Ala Phe Leu
        850                 855                 860
Ala Ile Pro Pro Thr Gln Phe Lys Leu Val Leu Asp Ser Ile Ile Trp
865                 870                 875                 880
Ala Phe Lys His Thr Met Arg Asn Val Ala Asp Thr Gly Leu Gln Ile
                885                 890                 895
Leu Phe Thr Leu Leu Gln Asn Val Ala Gln Glu Glu Ala Ala Ala Gln
        900                 905                 910
Ser Phe Tyr Gln Thr Tyr Phe Cys Asp Ile Leu Gln His Ile Phe Ser
        915                 920                 925
Val Val Thr Asp Thr Ser His Thr Ala Gly Leu Thr Met His Ala Ser
930                 935                 940
Ile Leu Ala Tyr Met Phe Asn Leu Val Glu Glu Gly Lys Ile Ser Thr
945                 950                 955                 960
Ser Leu Asn Pro Gly Asn Pro Val Asn Asn Gln Ile Phe Leu Gln Glu
                965                 970                 975
Tyr Val Ala Asn Leu Leu Lys Ser Ala Phe Pro His Leu Gln Asp Ala
        980                 985                 990
Gln Val Lys Leu Phe Val Thr Gly Leu Phe Ser Leu Asn Gln Asp Ile
        995                 1000                1005
Pro Ala Phe Lys Glu His Leu Arg Asp Phe Leu Val Gln Ile Lys Glu
    1010                1015                1020
Phe Ala Gly Glu Asp Thr Ser Asp Leu Phe Leu Glu Glu Arg Glu Ile
025                 1030                1035                1040
Ala Leu Arg Gln Ala Asp Glu Glu Lys His Lys Arg Gln Met Ser Val
                1045                1050                1055
Pro Gly Ile Phe Asn Pro His Glu Ile Pro Glu Glu Met Cys Asp
            1060                1065                1070
```

(2) INFORMATION FOR SEQ ID NO:2:

(i) SEQUENCE CHARACTERISTICS:
        (A) LENGTH: 3213 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
ATGCCAGCAA TTATGACAAT GTTAGCAGAC CATGCAGCTC GTCAGCTGCT TGATTTCAGC      60

CAAAAACTGG ATATCAACTT ATTAGATAAT GTGGTGAATT GCTTATACCA TGGAGAAGGA     120

GCCCAGCAAA GAATGGCTCA AGAAGTACTG ACACATTTAA AGGAGCATCC TGATGCTTGG     180
```

```
ACAAGAGTCG ACACAATTTT GGAATTTTCT CAGAATATGA ATACGAAATA CTATGGACTA    240

CAAATTTTGG AAAATGTGAT AAAAACAAGG TGGAAGATTC TTCCAAGGAA CCAGTGCGAA    300

GGAATAAAAA AATACGTTGT TGGCCTCATT ATCAAGACGT CATCTGACCC AACTTGTGTA    360

GAGAAAGAAA AGGTGTATAT CGGAAAATTA AATATGATCC TTGTTCAGAT ACTGAAACAA    420

GAATGGCCCA AACATTGGCC AACTTTTATC AGTGATATTG TTGGAGCAAG TAGGACCAGC    480

GAAAGTCTCT GTCAAAATAA TATGGTGATT CTTAAACTCT TGAGTGAAGA AGTATTTGAT    540

TTCTCTAGTG GACAGATAAC CCAAGTCAAA TCTAAGCATT TAAAAGACAG CATGTGCAAT    600

GAATTCTCAC AGATATTTCA ACTGTGTCAG TTTGTAATGG AAAATTCTCA AAATGCTCCA    660

CTTGTACATG CAACCTTGGA AACATTGCTC AGATTTCTGA ACTGGATTCC CCTGGGATAT    720

ATTTTTGAGA CCAAATTAAT CAGCACATTG ATTTATAAGT TCCTGAATGT TCCAATGTTT    780

CGAAATGTCT CTCTGAAGTG CCTCACTGAG ATTGCTGGTG TGAGTGTAAG CCAATATGAA    840

GAACAATTTG TAACACTATT TACTCTGACA ATGATGCAAC TAAAGCAGAT GCTTCCTTTA    900

AATACCAATA TTCGACTTGC GTACTCAAAT GGGAAAGATG ATGAACAGAA CTTCATTCAA    960

AATCTCAGTT TGTTTCTCTG CACCTTTCTT AAGGAACATG ATCAACTTAT AGAAAAAAGA   1020

TTAAATCTCA GGGAAACTCT TATGGAGGCC CTTCATTATA TGTTGTTGGT ATCTGAAGTA   1080

GAAGAAACTG AAATCTTTAA AATTTGTCTT GAATACTGGA ATCATTTGGC TGCTGAACTC   1140

TATAGAGAGA GTCCATTCTC TACATCTGCC TCTCCGTTGC TTTCTGGAAG TCAACATTTT   1200

GATGTTCCTC CCAGGAGACA GCTATATTTG CCCATGTTAT TCAAGGTCCG TTTATTAATG   1260

GTTAGTCGAA TGGCTAAACC AGAGGAAGTA TTGGTTGTAG AGAATGATCA AGGAGAAGTT   1320

GTGAGAGAAT TCATGAAGGA TACAGATTCC ATAAATTTGT ATAAGAATAT GAGGGAAACA   1380

TTGGTTTATC TTACTCATCT GGATTATGTA GATACAGAAA GAATAATGAC AGAGAAGCTT   1440

CACAATCAAG TGAATGGTAC AGAGTGGTCA TGGAAAAATT TGAATACATT GTGTTGGGCA   1500

ATAGGCTCCA TTAGTGGAGC AATGCATGAA GAGGACGAAA AACGATTTCT TGTTACTGTT   1560

ATAAAGGATC TATTAGGATT ATGTGAACAG AAAAGAGGCA AGATAATAA AGCTATTATT   1620

GCATCAAATA TCATGTACAT AGTAGGTCAA TACCCACGTT TTTTGAGAGC TCACTGGAAA   1680

TTTCTGAAGA CTGTAGTTAA CAAGCTGTTC GAATTCATGC ATGAGACCCA TGATGGAGTC   1740

CAGGATATGG CTTGTGATAC TTTCATTAAA ATAGCCCAAA AATGCCGCAG GCATTTCGTT   1800

CAGGTTCAGG TTGGAGAAGT GATGCCATTT ATTGATGAAA TTTTGAACAA CATTAACACT   1860

ATTATTTGTG ATCTTCAGCC TCAACAGGTT CATACGTTTT ATGAAGCTGT GGGGTACATG   1920

ATTGGTGCAC AAACAGATCA AACAGTACAA GAACACTTGA TAGAAAAGTA CATGTTACTC   1980

CCTAATCAAG TGTGGGATAG TATAATCCAG CAGGCAACCA AAAATGTGGA TATACTGAAA   2040

GATCCTGAAA CAGTCAAGCA GCTTGGTAGC ATTTTGAAAA CAAATGTGAG AGCCTGCAAA   2100

GCTGTTGGAC ACCCCTTTGT AATTCAGCTT GGAAGAATTT ATTTAGATAT GCTTAATGTA   2160

TACAAGTGCC TCAGTGAAAA TATTTCTGCA GCTATCCAAG CTAATGGTGA AATGGTTACA   2220

AAGCAACCAT TGATTAGAAG TATGCGAACT GTAAAAAGGG AAACTTTAAA GTTAATATCT   2280

GGTTGGGTGA GCCGATCCAA TGATCCACAG ATGGTCGCTG AAAATTTTGT TCCCCCTCTG   2340

TTGGATGCAG TTCTCATTGA TTATCAGAGA AATGTCCCAG CTGCTAGAGA ACCAGAAGTG   2400

CTTAGTACTA TGGCCATAAT TGTCAACAAG TTAGGGGGAC ATATAACAGC TGAAATACCT   2460

CAAATATTTG ATGCTGTTTT TGAATGCACA TTGAATATGA TAAATAAGGA CTTTGAAGAA   2520

TATCCTGAAC ATAGAACGAA CTTTTTCTTA CTACTTCAGG CTGTCAATTC TCATTGTTTC   2580
```

```
CCAGCATTCC TTGCTATTCC ACCTACACAG TTTAAACTTG TTTTGGATTC CATCATTTGG    2640

GCTTTCAAAC ATACTATGAG GAATGTCGCA GATACGGGCT TACAGATACT TTTTACACTC    2700

TTACAAAATG TTGCACAAGA AGAAGCTGCA GCTCAGAGTT TTTATCAAAC TTATTTTTGT    2760

GATATTCTCC AGCATATCTT TTCTGTTGTG ACAGACACTT CACATACTGC TGGTTTAACA    2820

ATGCATGCAT CAATTCTTGC ATATATGTTT AATTTGGTTG AAGAAGGAAA AATAAGTACA    2880

TCATTAAATC CTGGAAATCC AGTTAACAAC CAAATCTTTC TTCAGGAATA TGTGGCTAAT    2940

CTCCTTAAGT CGGCCTTCCC TCACCTACAA GATGCTCAAG TAAAGCTCTT TGTGACAGGG    3000

CTTTTCAGCT TAAATCAAGA TATTCCTGCT TTCAAGGAAC ATTTAAGAGA TTTCCTAGTT    3060

CAAATAAAGG AATTTGCAGG TGAAGACACT TCTGATTTGT TTTTGGAAGA GAGAGAAATA    3120

GCCCTACGGC AGGCTGATGA AGAGAAACAT AAACGTCAAA TGTCTGTCCC TGGCATCTTT    3180

AATCCACATG AGATTCCAGA AGAAATGTGT GAT                                 3213
```

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
TTCAATCTCT GGTAATCTAT GCCAGC                                           26
```

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GTAGTGTTCT TAAAGCACTA CAGCTTGG                                         28
```

(2) INFORMATION FOR SEQ ID NO:5:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CGGCTCGAGG CCCGGGGATC CATATGCCAG CAATTATGAC AATGTTAGC                 49
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GAGCGGATAA CAATTTCACA CAGG                                                    24

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Glu Phe Ala Gly Glu Asp Thr Ser Asp Leu Phe Leu Glu Glu Arg Glu
 1               5                  10                  15

Ile Ala Leu Arg
         20
```

HUMAN CRM1 PROTEIN

FIELD OF THE INVENTION

The present invention relates to a novel protein having the inhibitory function of transcription activity of a transcription factor and the like, and a DNA encoding it.

BACKGROUND OF THE INVENTION

The transcription factor AP-1 (activator protein-1) is a DNA binding protein complex composed of gene products of protooncogenes c-jun and c-fos and has been studied as a factor for controlling gene expression which is stimulated by a tumor promoter such as phorbol 12-myristate 13-acetate (PMA) or the like through the binding to its specific DNA sequence. Recently, it has been shown that, in addition to PMA, AP-1 activity is also controlled by various growth factors, cytokine, oncogene which causes transformation and ultraviolet light, and a close relation of AP-1 control to growth, differentiation and malignant alteration of cells has been reported (Biochimica et Biophysica Acta, 1072, 129–157 (1991)).

As an essential gene for maintaining the higher-order structure of a chromosome in *Schizosaccharomyces pombe*, crm1$^+$ (chromosome region maintenance) has been reported in 1989 (The Journal of Cell Biology, 108, 1195–1207 (1989)). This crm1$^+$ is essential for cell growth and a cold sensitive crm1 mutant of the fission yeast shows an abnormal nucleus morphology such as fiber or rod shape at the restrictive temperature. Further, it has such a character that it accumulates a large amount of a new protein of 25 kDa (p25) in the cells. This gene product is a protein composed of 1078 amino acid residues and localized in the nucleus (The Journal of Cell Biology, 108, 1195–1207 (1989)). The more recent study has shown that crm1$^+$ inhibits the activity of pap1$^+$ (pombe AP-1), which is a homologous gene of the transcription factor c-Jun/AP-1 of mammalian cells, in the fission yeast (Molecular and Cellular Biology, 12, 5474–5484 (1992)). The above-described p25 is one of genes whose transcriptions are controlled by pap1$^+$ and the accumulation of p25 protein in a large amount in the above mutant is considered to be caused by functional acceleration of pap1$^+$ due to functional defect of crm1$^+$. Furthermore, pap1$^+$ binding protein, pad1$^+$, has been newly found in the above yeast and this protein has been shown to have the function of promoting pap1$^+$ activity (Journal of Cell Science, 108, 569–579 (1995)). Recently, JAB1 gene, human homologous gene of pad1$^+$, has been isolated and it has been shown that the gene also accelerates the transcription activation capability of a jun family transcription activating factor in human cells by binding to the factor (Nature, 383, 453–457 (1996)).

OBJECTS OF THE INVENTION

One object of the present invention is to provide a protein having the inhibitory function of transcription activity of a transcription factor or the like, its partial peptide or their salts (hereinafter, sometimes, they are referred to as the protein, etc.).

Another object of the present invention is to provide an isolated DNA encoding the protein, etc.

A further object of the present invention is to provide a recombinant vector comprising the DNA and a transformant having the recombinant vector.

A further object of the present invention is to provide a process for preparing the protein.

Still another object of the present invention is to provide a pharmaceutical composition comprising the protein, etc. or the DNA.

Still another object of the present invention is to provide an antibody against the protein, etc.

Still another object of the present invention is to provide a method for screening for compounds which promote the function of the protein, etc., a screening kit and compounds obtained by the screening method.

These object as well as other objects and advantages of the present invention will become apparent to those skilled in the art from the following description with reference to the accompanying drawings.

BRIEF DESCRIPTION OF DRAWINGS

FIGS. 1A, 1B, 1C, 1D, 1E and 1F show a nucleotide sequence (SEQ ID NO:2) encoding the protein of the present invention obtained in Example 1 hereinafter and an amino acid sequence (SEQ ID NO:1) encoded by it.

SUMMARY OF THE INVENTION

Figure 2:
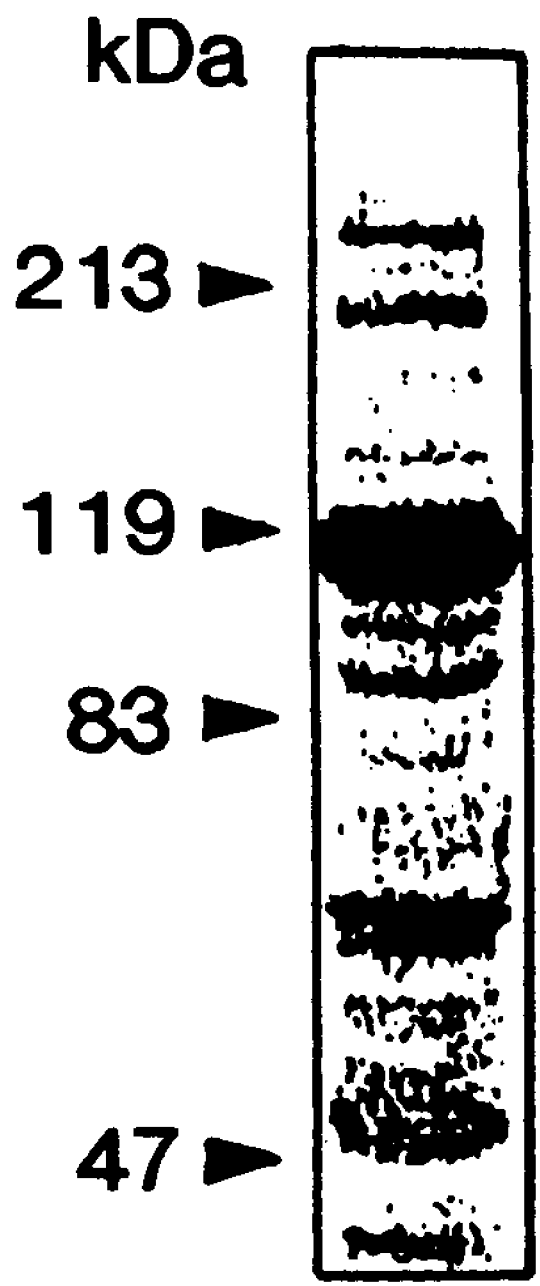
FIG. 2 illustrates the electrophoresis pattern obtained by Western blotting of HeLe cell protein in Example 4 hereinafter.

The present inventors have succeeded in cloning of a cDNA having a novel nucleotide sequence from a cDNA library derived from human myelocytic leukemia cell strain K562 cell, and have found that the protein encoded by it has the inhibitory function of transcription activity of transcription factors such as AP-1. As a result of the further study based on the present inventors' findings, the present invention has been completed.

That is, according to the present invention, there are provided:

(1) A protein which comprises the same or substantially the same amino acid sequence as that represented by SEQ ID NO:1, or its salt;

(2) The protein of the above (1) which is an inhibitory factor of a transcription factor;

(3) A partial peptide of the protein of the above (1) or its salt;

(4) An isolated DNA comprising DNA having a nucleotide sequence encoding the protein of the above (1) or the partial peptide of the above (3);

(5) The isolated DNA of the above (4) having the nucleotide sequence represented by SEQ ID NO:2;

(6) A recombinant vector comprising the DNA of the above (4);

(7) A transformant comprising the recombinant vector of the above (6);

(8) A process for preparing the protein of the above (1) or its salt which comprises cultivating the transformant of the above (7) to form and accumulate the protein of the above (1) or its salt and recovering it;

(9) A pharmaceutical composition which comprises the protein of the above (1), the partial peptide of the above (3) or a salt thereof;

(10) A pharmaceutical composition which comprises the isolated DNA of the above (4);

(11) The pharmaceutical composition of the above (10) or (11) for a prophylactic or therapeutic drug of a tumor;

(12) An antibody against the protein of the above (1), the partial peptide of the above (3) or a salt thereof;

(13) A method for screening for a compound which promotes the function of the protein of the above (1), the partial peptide of the above (3) or a salt thereof, or its salt which comprises using the protein of the above (1), the partial peptide of the above (3) or a salt thereof;

(14) The method for screening of the above (13), wherein the function to be promoted is the inhibitory function is of a transcription factor;

(15) A kit for screening for a compound which promotes the function of the protein of the above (1), the partial peptide of the above (3) or a salt thereof, or its salt which comprises as an essential component the protein of the above (1); the partial peptide of the above (3) or a salt thereof;

(16) The screening kit of the above (15), wherein the function to be promoted is the inhibitory function of a transcription factor; and

(17) A compound obtained by using the screening method of the above (13) or the screening kit of the above (15), or its malt.

DETAILED DESCRIPTION OF THE INVENTION

The protein of the present invention is that having the same or substantially the same amino acid sequence as that represented by SEQ ID NO:1.

The protein of the present invention may be any protein derived from any cells of human beings and other mammals (e.g., guinea pig, rat, mouse, rabbit, pig, sheep, cattle, monkey, etc.), for example, splenic cell, nerve cell, glia cell, β cell of pancreas, marrow cell, mesangial cell, Langerhans' cell, epidermic cell, epithelial cell, endothelial cell, fibroblast, fibrocyte, muscular cell, fat cell, immunocyte (e.g., macrophage, T cell, B cell, natural killer cell, mast cell, neutrophil, basophil, eosinophil, monocyte, etc.), megakaryocyte, synovial cell, chondrocyte, osteocyte, osteoblast, osteoclast, mammary gland cell, hepatocyte, or interstitial cell or their precursor cells, stem cells or cancer cells thereof and the like; and any tissues containing such cells, for example, brain, various parts of brain (e.g., olfactory bulb, amygdala, cerebral basal ganglia, hippocampus, thalamus, hypothalamus, substhanlamic nucleus, cerebral cortex, medulla, cerebellum), spinal cord, pituitary, stomach, pancreas, kidney, liver, genital organs, thyroid gland, gall bladder, bone marrow, adrenal gland, skin, muscle, lung, digestive tract, blood vessel, heart, thymus, spleen, submandibular gland, peripheral blood, intestinal tract, prostate, testicle, testis, ovarium, placenta, uterus, bone, joint and the like. And, the protein may be a synthetic one.

The wording "substantially the same amino acid sequence as that represented by SEQ ID NO:1" means an amino acid sequence having at least about 60% homology, preferably 70% to 80% homology, more preferably at least about 90% homology to the amino acid sequence represented by SEQ ID NO:1.

The protein of the present invention includes any protein which has substantially the same amino acid sequence as that represented by SEQ ID NO:1 and has an activity of substantially the same quality as that of the protein comprising the amino acid sequence represented by SEQ ID NO:1.

Examples of "an activity of substantially the same quality" include the inhibitory function of transcription activity of a transcription factor (transcription factor inhibitory function) and the like. The wording "substantially the same" means that the natures of their activities are equal to one another, qualitatively. Therefore, quantitative requirements such as degrees of the transcription factor inhibitory function and molecular weights of the proteins may differ from one another.

As the transcription factors, there may be mentioned a transcription factor which binds to a specific sequence of a DNA, a fundamental transcription factor which binds to a site about a promoter and the like. As the transcription factor which binds to a specific sequence of a DNA, there are, for example, transcription factors belonging to Jun family (e.g., c-Jun, JunD, JunB, v-Jun, etc.), transcription factors belonging to Fos family (e.g., c-Fos, FosB, Fra1, Fra2, v-Fos, etc.), AP-1 (complexes of transcription factors belonging to Jun family and those belonging to Fos family), nuclear receptors (receptors for retinoic acid or various fat soluble hormones), antioncognic products (e.g., p53 protein, etc.), NF-κB, CREB, E2F, CTF and the like. As the basic transcription factor which binds to a site about a promoter, there are, for example, TFIID (including TATA box binding protein), TFIIH and the like.

Further, the protein of the present invention may be a protein comprising a variant of the amino acid sequence represented by SEQ ID NO:1 having a deletion of one or more amino acids (e.g., about 2 to about 20, preferably about 2 to about 9, more preferably several amino acids (e.g., 1–5)), a variant of the amino acid sequence represented by SEQ ID NO:1 having an addition of one or more amino acids (e.g., about 2 to about 20, preferably about 2 to about 9, more preferably several amino acids (e.g., 1–5)), or a variant of the amino acid sequence represented by SEQ ID NO:1 having a substitution of one or more amino acids (e.g., about 2 to about 20, preferably about 2 to about 9, more preferably several amino acids (e.g., 1–5)), i.e., so-called muteins.

Furthermore, examples of the protein of the present invention include variants of the above protein, wherein the amino group of the N-terminal methionine residue of the above protein is protected with a protecting group (e.g., acyl group having 1 to 6 carbon atoms such as formyl group, acetyl group, etc.); the N-terminal region of the above protein is cleaved in a living body and the glutamyl group formed is pyroglutaminated; or a substituent (e.g., —OH, —SH, amino group, imidazole group, indole group, guanidino group, etc.) on the side chain of an amino acid in the molecule of the above protein is protected with a suitable protecting group (e.g., acyl group having 1 to 6 carbon atoms, for example, $C_{1-6}$ alkanoyl group, such as formyl group, acetyl group, etc.), or conjugated proteins of the above protein such as glycoproteins having sugar chains. The protein of the present invention is represented by a conventional manner in the peptide art. That is, the left hand end (amino terminal) is the N-terminal and the right hand end (carboxyl terminal) is the C-terminal. And, in the protein of the present invention, a representative example thereof being the protein comprising the amino acid sequence represented by SEQ ID NO:1, normally, the C-terminal is carboxyl group (—COOH) or carboxylate (—COO⁻), but the C-terminal may be the amide (—CONH$_2$) or an ester (—COOR).

Examples of R of the ester group include a $C_{1-6}$ alkyl group such as methyl, ethyl, n-propyl, isopropyl, n-butyl, etc., a $C_{3-8}$ cycloalkyl group such as cyclopentyl, cyclohexyl, etc., a $C_{6-12}$ aryl group such as phenyl, α-naphthyl, etc., a $C_{7-14}$ aralkyl group such as a phenyl-$C_{1-2}$ alkyl group (e.g., benzyl, phenethyl, etc.), an α-naphthyl- $C_{1-2}$ alkyl group (e.g., α-naphthylmethyl, etc.) and the like. In addition, pivaloyloxymethyl ester or the like which is used widely as an ester for oral administration can also be used.

When the protein of the present invention has a carboxyl group (or carboxylate) at a position other than the C-terminal, it may be amidated or esterified and such amide or ester is also included in the scope of the receptor protein of the present invention. The ester group may be the same group as that described with respect to the above C-terminal.

Examples of the protein of the present invention includes human protein (more specifically, that derived from human myelocytic leukemia cell strain K562 cell) having the amino acid sequence represented by SEQ ID NO:1 (the sequence of the 1st to the 1071st amino acids of FIGS. 1A, 1B, 1C, 1D, 1E and 1F.

As the salt of the protein of the present invention, in particular, a physiologically acceptable acid addition salt is preferred. Examples of the salt include those with inorganic acids (e.g., hydrochloric acid, phosphoric acid, hydrobromic acid, sulfuric acid, etc.) and those with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.).

The protein or its salt of the present invention can be produced from the above-described cells and tissues of human beings or other mammals by a per se known purification method of proteins. Alternatively, the protein or its salt of the present invention can be prepared by cultivating a transformant containing a DNA encoding the protein as described hereinafter, or according to a peptide synthesis method or its modification as described hereinafter.

When it is produced from cells or tissues of a human being or another mammal, the cells or tissues are homogenized and then extracted with, for example, an acid. The extract can be purified and isolated by combining chromatographies such as reverse phase chromatography, ion exchange chromatography and the like.

For synthesizing the protein or its salt of the present invention, normally, a commercially available synthetic resin for protein synthesis can be used. Examples of the resin include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymathylmethylphenylacetamidomethyl resin, polyacrylamide resin, 4-(2',4'-dimethoxyphenylhydroxymethyl)phenoxy resin, 4-(2',4'-dimethoxyphenyl-Fmoc aminoethyl) phenoxy resin and the like. By using such a resin and following the amino acid sequence of the desired protein, amino acids, wherein α-amino group and a functional group on a side chain are suitably protected, are condensed on the resin according to a per se known condensation method. After the condensation reaction, the protein is cleaved from the resin and, at the same time, various protecting groups are removed. Further, an intramolecular disulfide bond formation reaction is carried out in a highly dilute solution to obtain the desired protein or its amide isomer.

As for condensation of the above-described protected amino acids, various activating reagents for protein synthesis can be used. In particular, carbodiimides are preferred. Examples thereof include DCC, N,N'-diisopropylcarbodiimide, N-ethyl-N'-(3-dimethylaminoprolyl)carbodiimide and the like. For activation with the reagent, the protected amino acid can be added the resin together with a racemization-inhibiting additive (e.g., HOBt, HOOBt), directly. Alternatively, the protected amino acid is activated in advance in the form of a symmetric acid anhydride, HOBt ester or HOOBt ester and then the activated amino acid derivative can be added to the resin. As a solvent to be used for activation of protected amino acids and condensation with the resin, it can be appropriately selected from known solvents for protein condensation reactions. Examples thereof include acid amides such as N,N-dimethylformamide, N,N-dimethylacetamide, N-methylpyrrolidone and the like; halogenated hydrocarbons such as methylene chloride, chloroform and the like; alcohols such as trifluoroethanol and the like; sulfoxides such as dimethylsulfoxide and the like; ethers such as pyridine, dioxane, tetrahydrofuran and the like; nitrites such as acetonitrile, propionitrile and the like; esters such as methyl acetate, ethyl acetate and the like; suitable mixture of these solvents; and the like. The reaction temperature can be selected from those employed for peptide bond formation reactions, normally, within the range of from −20° C. to 50° C. Normally, the activated amino acid derivative is used in 1.5 times to 4 times excess amount. When insufficient condensation is indicated by ninhydrin reaction, condensation can be repeated without removal of protecting groups to obtain sufficient condensation. If sufficient condensation is not obtained by repetition of the condensation reaction, unreacted amino acids can be acetylated with acetic anhydride or acetylimidazole not to affect on the following reaction.

Examples of the protecting group for amino group of the starting material include Z, Boc, tert-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc and the like. The carboxyl group can be protected, for example, by alkyl esterification (esterification with straight, branched or cyclic alkyl such as methyl, ethyl, propyl, butyl, tert-butyl, cylcopentyl, cyclohexyl, cycloheptyl, cyclooctyl, 2-adamantyl, etc.), aralkyl esterification (formation of benzyl ester, 4-nitorbenzyl ester, 4-methoxybenzyl ester, 4-chlorobenzyl ester, benzhydril ester, etc.), phenacyl esterification, formation of benzyloxycarbonylhydrazide, formation of tert-butoxycarbonylhydrazide, formation of tritylhydrazide and the like.

The hydroxy group of serine can be protected, for example, by esterification or etherification. Suitable groups to be used for the esterification include, for example, lower alkanoyl groups such as acetyl group, aroyl groups such as benzoyl group, groups derived from carboxy acid such as benzyloxycarbonyl and ethoxycarbonyl, and the like. Suitable groups to be used for the etherification include, for example, benzyl, tetrahydropyranyl, t-butyl and the like.

As the protecting group for the phenolic hydroxy group of tyrosine, for example, Tos, 4-methoxy-2,3,6-trimethylbenzenesulfonyl, DNA, benzyloxymethyl, Bum, Boc, Trt, Fmoc and the like can be used.

Examples of the activated carboxyl group of the starting material include the corresponding acid anhydride, azide, activated ester (ester with an alcohol, e.g., pentachlorophenol, 2,4,5-trichlorophenol, 2,4-dinitrophenol, cyanomethylalcohol, p-nitrophenol, HONB, N-hydroxysuccinimide, N-hydroxyphthalimide, HOBt) and the like. Examples of the activated amino group of the starting material include the corresponding phosphoric acid amide.

Removal of the protecting group (deprotection) can be carried out, for example, by catalytic reduction in a stream of hydrogen in the presence of a catalyst such as Pd black or Pd-C; treatment with an acid, for example, anhydrous hydrogen fluoride, methanesulfonic acid, trifluoromethanesulfonic acid, trifluoroacetic acid, a mixture thereof and the like; by treatment with a base, for example, diisopropylethylamine, triethylamine, piperidine, piperazine and the like; reduction with sodium in liquid ammonia; and the like. The above treatment with an acid is generally carried out at about −20° C. to 40° C. and, in the treatment with an acid, addition of a cation scavenger such as anisole, phenol, thioanisole, m-cresol, p-cresol, dimethylsulfide, 1,4-butanediol, 1,2-ethanediol or the like is effective. Also, 2,4-dinitrophenyl group used for protecting the imidazole protecting group of histidine is removed by treatment with thiophenol, and formyl group used for protecting the indole protecting group of tryptophan can also be removed by treatment with an alkali such as a dilute sodium hydroxide solution, dilute ammonia, etc. in addition to the above acid treatment in the presence of 1,2-ethanediol, 1,4-butanediol, etc.

Known groups and means can be appropriately selected for protection of a functional group which should not participate in the reaction of the starting material and its protecting group as well as such conditions as removal of the protecting group, activation of a functional group which participates in the reaction, and the like.

Alternatively, the amide of the protein can be obtained, for example, by, first, protecting the α-carboxyl group of the C-terminal amino acid by amidation and extending a peptide (protein) chain towards the N-terminal to obtain the desired length of the chain. Then, only the protecting group of α-amino group of the N-terminal of the resultant peptide is removed to obtain a protein. Likewise, another protein is produced by removing only the protecting group of the C-terminal carboxyl group. Both ptomaine are condensed In the above-described mixed solvent. The condensation can be carried out as described above. The protected protein thus produced is purified and all the protecting groups can be deprotected as described above to obtain the desired crude protein. The crude protein can be purified by employing various known purification means and the main fraction is lyophilized to obtain the amide of the desired protein.

For obtaining an ester of the protein, for example, the α-carboxyl group of the C-terminal amino acid is esterified by condensation of the desired alcohol to obtain the corresponding amino acid ester. Then, according to the same manner as in the amide of the protein, the desired ester of the protein can be produced.

As the partial peptide of the protein of the present invention may be any partial peptide of the above-described proteins of the present invention. For example, there may be mentioned a peptide having an amino acid sequence composed of at least 10, preferably at least 50, more preferably at least 100 continuous amino acids in the amino acid sequence of the protein of the present invention. Specifically, the partial peptide having the amino acid sequences of the 86th to 940th amino acids of the amino acid sequence represented by SEQ ID NO:1 and the like are preferred.

Normally, the C-terminal of the partial peptide of the present invention is a carboxyl group (—COOH) or carboxylate (—COO⁻) and, like the protein of the present invention, the C-terminal may be the amide (—CONH$_2$) or ester (—COOR).

As the salt of the partial peptide of the present invention there may be mentioned the same salts as those described above with respect to the protein of the present invention.

The DNA encoding the protein of the present invention may be any DNA in so far as it contains the nucleotide sequence encoding the above-described protein of the present invention. The DNA may be any of genomic DNA, genomic DNA library, cDNA derived from the above-described cells and tissues, cDNA library derived from the above-described cells and tissues and synthetic DNA. The vector to be used for the library may be any of bacteriophage, plasmid, cosmid, phagemid and the like. In addition, the DNA can be amplified by reverse transcriptase polymerase chain reaction (hereinafter abbreviated to RT-PCR) with a mRNA fraction prepared from the above-described cells and tissues.

Specifically, the DNA encoding the protein having the amino acid sequence represented by SEQ ID NO:1 of the present invention may be, for example, the DNA having the nucleotide sequence represented by SEQ ID NO:2 or any DNA having a nucleotide sequence hybridizable to the nucleotide sequence represented by SEQ ID NO:2 under high stringent conditions and encoding a protein which has activities of the same quality, e.g., the transcription factor inhibitory function and the like as those of the protein having the amino acid sequence represented by SEQ ID NO:1. Examples of the hybridizable nucleotide sequence include nucleotide sequences having at least about 60%, preferably about 70% to about 80% homology, more preferably, at least about 90% homology to the nucleotide sequence represented by SEQ ID NO:2. As the transcription factor, there are the same factors as described above.

Hybridization can be carried out by a per se known method or its modification.

The high stringent conditions used herein are, for example, those of sodium concentration at about 19 mM to about 40 mM, preferably about 19 mM to about 20 mM and a temperature at about 50° C. to about 70° C., preferably about 60° C. to about 65° C. In particular, hybridization conditions of sodium concentration at about 19 mM and a temperature at about 65° C. are most preferred.

The DNA encoding the partial peptide of the present invention may be any DNA in so far as it contains the nucleotide sequence encoding the above-described partial peptide of the present invention. The DNA may be any of genomic DNA, genomic DNA library, cDNA derived from the above-described cells and tissues, cDNA library derived from the above-described cells and tissues and synthetic DNA. The vector to be used for the library may be any of bacteriophage, plasmid, cosmid, phagemid and the like. In addition, the DNA can be amplified by RT-PCR with a mRNA fraction prepared from the above-described cells and tissues.

Specifically, the DNA encoding the partial peptide having the sequence of the 86th to the 940th amino acids in the amino acid sequence represented by SEQ ID NO:1 is preferably the DNA having the sequence of the 256th to the 2820th bases in the nucleotide sequence represented by SEQ ID NO:2 or the like.

As the means for cloning the DNA encoding the protein, etc. of the present invention, there is amplification of the desired DNA from the above-described DNA library or the like by PCR using synthetic DNA primers containing partial nucleotide sequences of the protein of the present invention. Alternatively, DNA integrated into a suitable vector is selected by hybridization with labeled DNA fragment or a synthetic DNA encoding a part or entire region of the protein of the present invention. The hybridization is carried out, for example, according to the method described in Molecular Cloning 2nd ed.; J. Samrook et al., Cold Spring Harbor Lab. Press, (1989). A commercially available library can be used according to the direction of the attached manufacturer's protocol.

The cloned DNA encoding the protein, etc. of the present invention can be used as such according to a particular purpose. Alternatively, if desired, it can be used after digestion with one or more restriction enzymes, or a linker can be added. The DNA may have the codon, ATG, as a translation initiation codon at its 5' terminal side and the codon, TAA, TGA or TAG as a translation termination codon at its 3' terminal side. These translation initiation and termination codons can be added by using a suitable synthetic DNA adapter.

The expression vector of the protein, etc. of the present invention can be prepared, for example, by (a) cutting out the desired DNA fragment from the DNA encoding the protein of the present invention and (b) joining the DNA fragment to a suitable expression vector at the downstream from a promoter in the vector.

Examples of the vector include plasmids derived form E. coli (e.g., pBR322, pBR325, pUC12, pUC13), plasmids derived from Bacillus subtilis (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter in so far as it matcher with a host to be used for gene expression. In case of using animal cells as the host, examples of the promoter include CMV promoter, SRα promoter, SV40 promoter, LTR promoter, HSV-TK promoter, CAG promoter, etc. Among them, CMV promoter or SRα promoter is preferred. In case of using bacteria of the genus Escherichia as the host, preferred examples of the promoter include trp promoter, T7 promoter, lac promoter, recA promoter, $\lambda P_L$ promoter, lpp promoter, etc. In case of using bacteria of the genus Bacillus as the host, preferably, SPO1 promoter, SPO2 promoter, penP promoter, etc. can be used. In case of using yeast as the host, preferred examples of the promoter Include PHO5 promoter, PGK promoter, GAP promoter, ADH1 promoter, GAL promoter, etc. In case of using insect cells as the host, preferred examples of the promoter include polyhedrin prompter, P10 promoter, etc.

In addition to the above, optionally, the expression vector may further contains enhancer, splicing signal, poly A addition signal, selection marker, SV40 replication origin (hereinafter sometimes abbreviated to SV40 ori), etc. Examples of the selection marker include dihydrofolate reductase (hereinafter sometimes abbreviated to dhfr) gene [methotrexate (MTX) resistance], ampicillin resistant gene (hereinafter sometimes abbreviated to Amp$^r$), neomycin resistant gene (hereinafter sometimes abbreviated to Neo, G418 resistance), etc. In particular, when CHO (dhfr$^-$) cell Is used together with DHFR gene as a selection marker, selection can also be carried out by using a thymidine free medium.

If necessary, a signal sequence which matches with a host Is added to the N-terminal side of the protein of the present invention. As the signal sequence, there may be mentioned phoA signal sequence, ompA signal sequence, etc. in case of using bacteria of the genus Escherichia as the host; α-amylase signal sequence, subtilisin signal sequence, etc. in case of using bacteria of the genus Bacillus as the host; MFα signal sequence, SUC2 signal sequence, etc. in case of using yeast as the host; insulin signal sequence, α-interferon signal sequence, antibody molecule signal sequence, etc. in case of using animal cells as the host, respectively.

The DNA encoding the protein of the present invention thus constructed can be introduced into a host to produced a transformant.

As the host, for example, there may be mentioned bacteria of the genus Escherichia, bacterial of the genus Bacillus, yeast, insect cells, insects and animal cells, etc.

Specific examples of bacteria of the genus Escherichia include Escherichia coli K12 DH1 [Proc. Natl. Acad. Sci. USA, 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of bacteria of the genus Bacillus include Bacillus subtilis MI114 [Gene, 24, 255 (1983)], 207–21 [Journal of Biochemistry, 95, 87 (1984)], etc.

Examples of yeast include Saccharomyces cereviseae AH22, AH22$^-$, NA87-11A, DKD-5D, 20B-12, etc. and Schizosaccharomyces pombe NCYC1913, NCYC2036, etc.

Examples of insect cells include Spodoptera frugiperda cell (Sf cell), MG1 cell derived from mid-intestine of Trichoplusia ni, High Five™ cell derived from egg of Trichoplusia ni, cells derived from Mamestra brassicae, cells derived from Estigmena acrea, etc. for the virus, AcNPV; and Bombyx mori N cell (BmN cell), etc. for the virus, BmNPV. As the Sf cell, for example, Sf9 cell (ATCC CRL1711) and Sf21 cell described by Vaughn, J. L., in Vitro, 13, 213–217 (1977) can be used.

As the insect, for example, a larva of Bombyx mori can be used [Maeda et al., Nature, 315, 592 (1985)].

Examples of animal cells include monkey cell COS-7, Vero cell, Chinese hamster cell CHO (hereinafter abbreviated to CHO cell), dhfr gene deficient Chinese hamster cell CHO (hereinafter abbreviated to CHO (dhfr$^-$) cell), L cell, myeloma cell, human FL cell, 293 cell, C127 cell, mouse cell, BALB3T3 cell, Sp-2/0 cell, etc. Among them, CHO cell, CHO (dhfr$^-$) cell, 293 cell, etc. are preferred.

Transformation of bacteria of the genus Escherichia is carried out, for example, according to the method described in Proc. Natl. Acad. Sci. USA, 69, 2110 (1972) or Gene, 17, 107 (1982).

Transformation of bacteria of the genus Bacillus is carried out, for example, according to the method described in Molecular & General Genetics, 168, 111 (1979).

Transformation of yeast is carried out, for example, the method described in Methods in Enzymology, 194, 182–187 (1991).

Transformation of insect cells or insect is carried out, for example, according to the method described in Bio/Technology, 6, 47–55(1988).

Transformation of animal cells is carried out, for example, according to the method described in Saiboukogaku (Cell Technology) Separate-Volume 8, New Cell Technology Experimental Protocol, 263–267 (1995), published by Syuzyunsha.

Introduction of the expression vector into cells can be carried out, for example, by lipofection (Felgner, P. L. et al., Proc. Natl. Acad. Sci. USA, 84, 7413 (1987)), calcium phosphate method (Graham, F. L. and van der Eb, A. J., Virology, 52, 456–467 (1973)), electroporation (Nuemann, E. et al., EMBO J., 1, 841–845 (1982)) or the like.

Thus, the transformant transformed with the expression vector containing the DNA encoding the protein, etc. of the present invention can be obtained.

As a method for expression of the protein, etc. of the present invention stably by using an animal cell, there may be mentioned clone selection for selecting an animal cell wherein the expression vector introduced is integrated in its chromosome. More specifically, a transformant is selected by utilizing the above selection marker as an indicator. Further, clone selection of thus-obtained animal cells by using the above selection marker can be carried out repeatedly to obtain a stable animal cell strain which has high expressibility of the protein, etc. of the present invention. When using dhfr gene as the selection marker, an animal cell strain having higher expressibility can be obtained by cultivating the cell with gradually increasing MTX concentration to select a resistant strain, thereby amplifying the DNA encoding the protein, etc. of the present invention together with dhfr gene in the cell.

The protein, etc. of the present invention can be produced by cultivating the above-described transformant under such conditions that the DNA encoding the protein, etc. of the present invention can be expressed to form and accumulate the protein, etc. of the present invention.

In case of the bacterial host of the genus Escherichia or Bacillus, the transformant can be suitably cultivated in a liquid culture medium and materials required for growth of the transformant such as carbon sources, nitrogen sources, inorganic materials, etc. are added to the medium. Examples of the carbon sources include glucose, dextrin, soluble starch, sucrose, etc. The nitrogen sources include, for example, inorganic or organic materials such as ammonium salts, nitrate salts, corn steep liquor, peptone, casein, meat extract, soybean meal, potato extract, etc. The inorganic materials include, for example, calcium chloride, sodium dihydrogen phosphate, magnesium chloride, etc. In addition, yeast extract, vitamins, growth promoting factors etc. can be added. Preferably, the medium is adjusted to pH about 5 to about 8.

Preferably, the medium for cultivating the bacteria of the genus Escherichia is, for example, M9 medium containing glucose and Casamino Acids (Miller, Journal of Experiments in Molecular Genetics, 431–433, Cold Spring Harbor Laboratory, New York, 1972). If necessary, in order to activate the promoter efficiently, for example, an agent such as 3β-indolyl acrylic acid can be added to the medium.

In case of the bacterial host of the genus Escherichia, normally, the transformant is cultivated at 15° C. to about 43° C. for about 3 hours to about 24 hours. If necessary, the culture can be aerated or stirred.

In case of the bacterial host of the genus Bacillus, normally, the transformant is cultivated at about 30° C. to about 40° C. for about 6 hours to about 24 hours. If necessary, the culture can be aerated or stirred.

In case of the yeast host, the transformant is cultivated in, for example, Burkholder's minimal medium [Bostian, K. L. et al., Proc. Natl. Acad. Sci. USA, 77, 4505 (1980)] and SD medium containing 0.5% Casamino Acids [Bitter, G. A., Proc. Natl. Acad. Sci. USA, 81, 5330 (1984)]. Preferably, the medium is adjusted to pH about 5 to about 8. Normally, the transformant is cultivated at about 20° C. to about 35° C. for about 24 hours to about 72 hours. If necessary, the culture can be aerated or stirred.

In case of the insect cell host or insect host, the transformant is cultivated in, for example, Grace's Insect Medium [Grace, T. C. C., Nature, 195, 788 (1962)] to which an appropriate additive such as inactivated 10% bovine serum is added. Preferably, the medium is adjusted to pH about 6.2 to about 6.4. Normally, the transformant is cultivated at about 27° C. for 3 days to 5 days and, if necessary, the culture can be aerated or stirred.

In case of the animal cell host, the transformant is cultivated in, for example, MEM medium containing about 5% to about 20% fetal bovine serum [Science, 122, 501 (1952)], DMEM medium [Virology, 8, 396 81959)], RPMI 1640 medium [The Journal of the American Medical Association, 199, 519 (1967)], 199 medium [Proceeding of the Society for the Biological Medicine, 73, 1 (1950)], etc. Preferably, the medium is adjusted to pH about 6 to about 8. Normally, the transformant is cultivated at about 30° C. to about 40° C. for about 15 hours to about 72 hours and, if necessary, the culture can be aerated or stirred.

In particular, when using CHO (dhfr⁻) cell and dhfr gene as a selection marker, it is preferred to use DMEM medium which contains dialyzed fetal bovine serum almost free from thymidine.

Separation and purification of the protein, etc. of the present invention from the above culture can be carried out, for example, as follows.

For extraction of the protein, etc. of the present invention from the transformant culture, a known method can be appropriately employed. For example, after cultivation, the transformant is recovered by a per se known method and suspended in a suitable buffer. Then, the transformant is disrupted by ultrasonication, treatment with lysozyme and/or freeze-thaw cycling, followed by separating a crude extract of the protein, etc. of the present invention by centrifugation, filtration, etc. The buffer may contain a protein modifier such as urea, guanine hydrochloride or a surfactant such as Triton X-100™ (TM means the registered trademark), etc.

When the protein is secreted in the culture broth, after completion of cultivation, its supernatant can be separated from the transformant cells by a per se known method to collect the supernatant.

Purification of the protein, etc. of the present invention contained in the culture supernatant thus obtained or the extract can be carried Out by combining per se known separation and purification methods appropriately. As the per se known separation and purification methods, there may be mentioned a method utilizing difference in solubilities such as salting out, solvent precipitation, etc.; a method mainly utilizing difference in molecular weights such as dialysis, ultrafiltration, gel filtration, SDS-polyacrylamide gel electrophoresis, etc.; a method utilizing difference in electric charges such as ion exchange chromatography, etc.; a method utilizing difference in specific affinities such as affinity chromatography, etc.; a method utilizing difference in hydrophobic properties such as reverse phase high performance liquid chromatography, etc.; a method utilizing difference in isoelectric points such as isoelectric point electrophoresis; and the like.

When the protein, etc. of the present invention is obtained in its free form, it can be converted into its salt by a per se known method or its modification. On the other hand, when the protein, etc. of the present invention is obtained in the form of a salt, it can be converted into the free form or a different salt by a per se known method or its modification.

The protein, etc. of the present invention produced by the recombinant can be treated with an appropriate protein modifying enzyme prior to or after purification to appropriately modify the protein or to partially remove a polypeptide. Examples of the protein modifying enzyme include trypsin, chymotrypsin, arginyl endopeptidase, protein kinase, glycosidase and the like.

The presence of thus-produced protein, etc. of the present invention can be determined by an enzyme immunoassay using a specific antibody.

The protein, its partial peptide or their salts can be produced according to a per se known peptide synthetic method, or by cleaving the protein of the present invention with a suitable peptidase. As the peptide synthesis method, for example, any of solid phase synthesis and liquid phase synthesis can be employed. That is, the desired peptide can be produced by condensing a partial peptide or amino acid sequence which can compose of the protein of the present intention with the remaining part and deprotecting a protecting group, if any. Conventional condensing methods and deprotecting methods can be employed and they are described by, for example, M. Bodanszky and M. A. Ondetti, Peptide Synthesis, Interscience Publishers, New York (1966); Schroeder and Luebke, the Peptide, Academic Press, New York (1965); Nobuo Izumi et al., Fundamental and Experiment of Peptide Synthesis, Maruzen (1975); Haruaki Yazima and Syunpei Skakibara, Biochemistry Experiment Lecture, Protein Chemistry IV, 205 (1977); Haruaki Yazima, Second Series Drug Development Vol. 14, Peptide Synthesis, Hirokawa Shoten.

After completion of the reaction, the protein of the present invention can be purified and isolated by combining conventional purification methods such as solvent extraction, distillation, column chromatography, liquid chromatography, recrystallization and the like. In case the protein thus obtained is a free protein, it can be converted into its appropriate salt according to a known method. On the other hand, the protein obtained is in the form of a salt, it can be converted into the corresponding free protein.

An antibody against the protein, etc. of the present invention may be any monoclonal or polyclonal antibody in so far as it can recognize the protein, etc. of the present invention. The antibody against the protein, etc. of the present invention can be produced by using the protein, etc. of the present invention as the antigen according to a conventional antibody or antiserum preparation process.

Preparation of Monoclonal Antibody (a) Preparation of monoclonal antibody producer cells The protein, etc. of the present invention as such or together with a suitable carrier or diluent is administered to a site of a mammal which permits the antibody production. For enhancing the antibody production capability, complete Freund's adjuvant or incomplete Freund's adjuvant may be administered. Normally, the protein, etc. is administered once every 2 weeks to 6 weeks, in total, about 2 times to is about 10 times. The mammal to be used include-monkey, rabbit, dog, guinea pig, mouse, rat, sheep, goat and the like and mouse or rat is preferred.

For preparing monoclonal antibody-producing cells, an individual whose antibody titer has been confirmed is selected from warm blood animals immunized with the antigen, for example, mouse and, 2 days to 5 days after the final immunization, its spleen or lymph node is collected and antibody-producing cells contained therein are fused with myeloma cells to prepare the desired monoclonal antibody producer hybridoma. Measurement of the antibody titer in an antiserum can be carried out, for example, by reacting the labeled protein, etc. as described hereinafter and an antiserum and then measuring the activity of the labeling agent bound to the antibody. The cell fusion can be carried out according to a known method, for example, the method described by Koehler and Milstein, Nature, 256, 495 (1975). As a fusion promoter, for example, polyethylene glycol (PEG) or Sendai virus (HVJ), preferably PEG can be used.

Examples of myeloma cells include NS-1, P3U1, SP2/0, AP-1 and the like, and P3U1 is preferred. The proportion of the number of antibody producer cells (spleen cells) and the number of myeloma cells to be used is preferably about 1:1 to about 20:1 and PEG (preferably PEG 1000–PEG 6000) is added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods can be used for screening for a hybridoma producing the antibody against the protein, etc. For example, there may be mentioned a method wherein a Supernatant of the hybridoma is added to a solid phase (e.g., microplate) to which the protein, etc. antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein, etc. bound to the solid phase; and a method wherein a supernatant of the hybridoma is added to a solid phase to which an anti-immunoglobulin antibody or Protein A is adsorbed and then the protein, etc., labeled with a radioactive substance or an enzyme is added to detect the monoclonal antibody against the protein, etc. bound to the solid phase.

Selection of the monoclonal antibody can be carried out according to a per se known method or its modification. Normally, a medium for animal cells to which HAT (hypoxanthine, aminopterin, thymidine) are added is employed. Any selection and growth medium can be employed in so far as the hybridoma can grow. For example, RPMI 1640 medium containing 1% to 20%, preferably 10% to 20% fetal bovine serum, GIT medium containing 1% to 10% fetal bovine serum (Wako Pure Chemical Industries, Ltd.), a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein, etc. in the antiserum.

(b) Purification of monoclonal antibody

Separation and purification of a monoclonal antibody against the protein, etc. can be carried out according the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Preparation of Polyclonal Antibody

A polyclonal antibody against the protein, etc. of the present invention can be prepared by a per se known method or its modification. For example, a complex of an immunogen (an antigen against the protein, etc.) and a carrier protein is prepared and a mammal is immunized by the complex according to the same manner as that described with respect to the above monclonal antibody preparation. A material containing the antibody against the protein, etc. of the present invention is recovered from the immunized animal and the antibody is separated and purified.

As to the complex of the immunogen and the carrier protein to be used for immunization of a mammal, any carrier protein and any mixing proportion of the carrier and a hapten can be employed in so far as an antibody against the hapten, which is crosslinked on the carrier and used for immunization, is produced efficiently. For example, bovine serum albumin, bovine cycloglobulin, keyhole limpet hemocyanin, etc. can be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, there may be mentioned glutaraldehyde, carbodiimide, maleimide activated ester, activated ester reagents containing thiol group or dithiopyridyl group, and the like. The condensation product as such or together with a suitable carrier or diluent is administered to a site of a mammal which permits the antibody production. For enhancing the antibody production capability, complete Freund's adjuvant or incomplete Freund's adjuvant may be administered. Normally, the protein, etc. is administered once every 2 weeks to 6 weeks, in total, about 3 times to about 10 times.

The polyclonal antibody is recovered from blood, ascites and the like, preferably, blood of an animal immunized by the above method.

The antibody titer of the anti-protein, etc. in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein, etc. of the present invention has the inhibitory function of transcription activity of a transcription factor and the like and it is useful as an inhibitory factor of a transcription factor.

Examples of the transcription factor include a transcription factor which binds to a specific sequence of a DNA, a basal transcription factor which binds to about a promoter and the like. As a transcription factor which binds to a specific sequence of a DNA, for example, there are transcription factors belonging to Jun family (e.g., c-Jun, JunD, JunB, v-Jun), transcription factors belonging to Fos family (e.g., c-Fos, FosB, Fra1, Fra2, v-Fos), AP-1 (a complex of a transcription factor of Jun family and a transcription factor of Fos family), nuclear receptors (receptors for retinoic acid and various hydrophobic hormones), antioncogenic product (e.g., p53 protein), NF-κB, CREB, E2F, CTF and the like. As a basal transcription factor which binds to about a promoter, for example, there are TFIID (containing TATA box binding protein), TFIIH and the like. Among them, AP-1 and the like are preferred.

Therefore, the protein, etc. of the present invention can be used for various utilities.

Hereinafter, utilities of the protein, its partial peptide and their salts of the present invention, DNAs encoding them of the present invention, the antibody and oligonucleotides and their derivatives of the present invention will be illustrated.

(1) Drugs

For example, the protein, its partial peptide and their salts of the present invention and the DNA encoding the protein or its partial peptide of the present invention are useful as drugs for prophylaxis and therapy of deficiency of the gene encoding the protein of the present invention or diseases caused by such deficiency, or functional depression of the protein of the present invention or diseases caused by such depression. Specifically, they are useful as drugs for prophylaxis and therapy of tumors (e.g., cancer such as bladder carinoma, breast cancer, cancer of uterine carvix, cancer of large intestine (carcinoma of colon and rectum), lung cancer, non-small cell lung cancer, ovarian cancer, prostatic cancer, small cell lung cancer, gastric cancer, etc., chronic lymphocytic leukemia, chronic myelogenous leukemia, malignant melanoma, metastasis, multiple myeloma, non-Hodgkin lymphoma, etc.), acute bacterial periostitis, acute myocardial infarction, acute pancreatitis, acute viral encephalitis, adult respiratory distress syndrome, rigid spondylitis, bacterial pneumonia, chronic pancreatitis, gastritis, hepatitis A, hepatitis B, hepatitis C, herpes simplex infection, varcella-zoater virus infection, Hodgkin disease, AIDS infection, human papillomavirus infection, influenza virus infection, active staphylococcal infection, osteoarthritis, bone atropy (prophylaxis of osteoporosis), osteoporosis, bone Behcet disease, pain, peptic ulcer, peripheral vessel disease, rheumatoid arthritis, septic shock, systemic mycosis, valvular disease of heart and the like, in particular, tumors.

The protein, etc. of the present invention or the DNA encoding them can be used in the form of tablets, if necessary, providing sugar coating, capsules, elixirs, microcapsules, etc. for oral administration, or in the for of injectable preparations such as aseptic solutions or suspensions in water or other pharmaceutically acceptable solutions for parenteral administration. A pharmaceutical composition in a unit dosage form can be prepared by mixing the DNA of the present invention with, for example, one or more pharmaceutically acceptable carriers, flavors, excipients, vehicles, preservatives, Stabilizers, binders, etc. according to generally acceptable manner. The effective component is contained in the composition in such an amount that a dose in the intended desired range can be obtained.

In case of the DNA of the present invention is used, it can be used alone or, after inserted into a suitable vector such as retroviral vector, adenoviral vector, adenovirus associated viral vector, etc. according to a conventional method.

Examples of additives to be mixed in tablets; capsules, etc. include binders such as gelatin, corn starch, tragacanth gum and gum arabic, excipients such as crystalline cellulose, swelling agents such as corn starch, gelatin and alginic acid, lubricants such as magnesium stearate, sweetenings such as sucrose, lactose and saccharin, flavors such as peppermint, akamono oil and cherry, and the like. In case of the capsule dosage unit form, in addition to the above component, it can contain a liquid carrier such as fat or oil. An injectable aseptic composition can be prepared according to a conventional manner, for example, by dissolving or suspending the active component in a vehicle ouch as injectable water and a natural vegetable oil such as sesame oil, coconut oil, etc. Examples of the injectable aqueous solution include physiological saline, isotonic solutions containing glucose and other adjuvants (e.g., D-sorbitol, D-mannitol, sodium chloride, etc.) and suitable dissolution aids, for example, alcohols (e.g., ethanol), polyalcohols (e.g., propylene glycol, polyethylene glycol), nonionic surfactants (e.g., Polysorbate 80™, HCO-50) may be further added. As an oily solution, for example, sesame oil, soybean oil, etc. can be used and a dissolution aid such as benzyl benzoate or benzyl alcohol, etc. can be further added. The above prophylactic and therapeutic drugs can further contain, for example, buffers (e.g., phosphate buffer, sodium acetate buffer), smoothing agents (e.g., benzalkonium chloride, procaine hydrochloride, etc.), stabilizers (e.g., human serum albumin, polyethylene glycol, etc.), preservatives (e.g., benzyl alcohol, phenol, etc.), antioxidants, and the like. The injectable preparation thus produced is normally filled in a suitable ampoule.

Since the pharmaceutical composition thus obtained is safe and low toxic, it can be administer to a human being and another mammal (e.g., rat, rabbit, sheep, pig, cattle, .horse, cat, dog, monkey, etc.).

Although the amount of the protein, etc. or DNA of the present invention to be administered is varied according to particular diseases, etc., in general, for oral administration to an adult human being (as 60 kg body weight), it is administered in an amount of about 0.1 mg/day to about 100 mg/day, preferably about 1.0 mg/day to about 50 mg/day, more preferably about 1.0 mg/day to about 20 mg/day. For parenteral administration to an adult human tumor patient (as 60 kg body weight), it is advantageous to administer the composition in the form of an injectable preparation in an amount of about 0.01 mg/day to about 30 mg/day, preferably about 0.1 mg/day to about 20 mg/day, more preferably about 0.1 mg/day to about 10 mg/day, though the single dosage is varied according to particular diseases, routes of administration, etc. As to other animals, the composition can be administered in the above amount with converting it into that for the body weight of 60 kg.

(2) Gene diagnosing agent

The DNA encoding the protein, etc. of the present invention can be used for detecting an abnormality of DNA or mRNA encoding the protein or the partial peptide of the present invention (hereinafter abbreviated to DNA or mRNA of the present invention) (abnormal gene) in a human being or another mammal (e.g., rat, rabbit, sheep, pig, cattle, horse, cat, dog, monkey, etc.). Therefore, it is useful as a gene diagnosing agent for detecting, for example, damage, mutation or lowering of expression of the DNA or mRNA of the present invention, increased or excess expression of the DNA or mRNA of the present invention and the like.

The gene diagnosis using the DNA or mRNA of the present invention can be carried out, for example, by a per se known Northern hybridization, PCR-SSCP method (Genomics, 5, 874–879 (1989); Proc. Natl. Acad. Sci. USA, 86, 2766–2770 (1989)), or the like. For example, when lowering of expression is detected by Northern hybridization or mutation of DNA is detected by PCR-SSCP method, one can diagnose that probability of a tumor and the like is very high.

(3) Determination of the protein, etc. of the present invention

Since the antibody against the protein, etc. of the present invention can recognize the protein, etc. of the present invention specifically, it can be used for quantitative determination of the protein, etc. of the present invention in a specimen fluid, in particular, determination by a sandwich immunoassay or the like.

That is, the present invention provides:

(a) a method for determining the protein, etc. of the present invention in a specimen fluid which comprises reacting the antibody against the protein, etc. of the present invention with the specimen fluid and the labeled protein, etc. of the present invention, competitively, and measuring the proportion of the labeled protein, etc. of the present invention bound to the antibody; and (b) a method for determining the protein, etc. of the present invention in a specimen fluid which comprises reacting the specimen fluid with one antibody of the present invention insolubilized on a carrier and another labeled antibody of the present invention, simultaneously or continuously and measuring the activity of the labeling agent on the insolubilized carrier.

In the determination of the above (b), preferably, one antibody recognizes the N-terminal of the protein, etc. of the present invention and the other antibody reacts with the C-terminal of the protein, etc. of the present invention.

In addition to the determination of the protein, etc. of the present invention, the monoclonal antibody against the protein, etc. of the present invention (hereinafter sometimes referred to as anti-protein antibody) can be used for detection by histological stains and the like. For these purposes, the antibody molecule as such can be used or $F(ab')_2$, Fab' or Fab fraction of the antibody molecule can also be used.

A method for determination using an antibody against the receptor protein, etc. of the present invention is not specifically limited and any determination method can be used in so far as an amount of an antigen (e.g., an amount of protein), antibody or antibody-antigen complex corresponding to an amount of an antigen in a fluid to be determined can be detected by a chemical or physical means and calculated based on a calibration curve prepared by using standard solutions containing known amounts of the antigen. For example, nephelometry, competitive method, immunometric method and sandwich method are suitably employed. In particular, in view of sensitivity, specificity and the like, a sandwich method as described hereinafter is preferred.

As a labeling agent used in a determination method using a labeled reagent, radioisotopes, enzymes, fluorescent materials, luminous materials and the like can be used. Examples of radioisotopes include $[^{125}I]$, $[^{131}I]$, $[^{3}H]$, $[^{14}C]$ and the like. As the above enzymes, that having good stability and high specific activities is preferred and, for example, there are β-galactosidase, β-glucosidase, alkaline phosphatase, peroxidase, malate dehydrogenase and the like. As the fluorescent materials, for example, there are fluorescamine, fluorescein isothiocyanate and the like. As the luminous materials, there are luminol, luminol derivatives, luciferin, lucigenin and the like. In addition, biotin-avidin system can be used for binding of an antibody or antigen to a labeling agent.

For insolubilization of an antigen or antibody, physical adsorption can be used or, normally, a method using a chemical bond for insolubilizing or immobilizing a protein or an enzyme can be used. Examples of the carrier include insoluble polysaccharides such as agarose, dextran, cellulose and the like, synthetic resins such as polystyrene, polyacrylamide, silicone and the like, glass and the like.

In a sandwich method, a specimen fluid to be tested is reacted with an insolubilized anti-protein antibody (primary reaction) and further reacting a labeled anti-protein antibody (secondary reaction), followed by measuring the labeling agent on the insoluble carrier to determine the amount of the protein, etc. of the present invention in the specimen fluid. The order of the primary and secondary reactions can be reversed and they can be carried out simultaneously or separately at different times. The above-described labeling agent and insolubilization can be applied to this method. In addition, in an immunoassay by a sandwich method, an antibody to be used as the solid phase antibody or labeled antibody is not necessary one kind of antibodies and, in order to improve measuring sensitivity, etc., a mixture of two or more kinds of antibodies can be used.

In the method for determination of the protein, etc. of the present invention by the sandwich method of the present invention, preferably, the antibodies against the protein, etc. used in the primary and secondary reactions are those having different binding sites for the receptor protein. For example, when the antibody used in the secondary reaction is that recognizing the C-terminal region of the protein, etc., preferably, the antibodies used in the primary reaction is that recognizing an region other than the C-terminal region, for example, the N-terminal region.

The antibody against the protein, etc. of the present invention can also be used for a measuring system other than a sandwich methods for example, a competitive method, immunometric method, nephelometry and the like. In a competitive method, an antigen in a specimen fluid and a labeled antigen are reacted with the antibody competitively and, after separation of the unreacted labeled antigen (P) from the labeled antigen bound to the antibody (B)t measuring the amount of the labeling agent of either B or P to determine the amount of the antigen in the specimen fluid. In this reaction, both liquid phase method and solid phase method can be employed. In the liquid phase method, a soluble antibody is used as the antibody and B/F separation can be carried out by using polyethylene glycol, a second antibody against the above antibody. In the solid phase method, an immobilized solid phase antibody is used as the first antibody, or a soluble antibody is used as the first antibody and an immobilized solid phase antibody is used as the second antibody.

In the immunometric method, an antigen in a specimen fluid to be tested and an immobilized solid phase antigen are reacted with a given amount of a labeled antibody, competitively and then the solid phase is separated from the liquid phase. Alternatively, an antigen in a specimen fluid to be tested is reacted with an excess amount of a labeled antibody and an immobilized solid phase antigen is added to permit the unreacted labeled antibody to bind to the solid phase, followed by the separation of the solid phase from the liquid phase. Then, the amount of the labeling agent of either phase is measured to determine the amount of the antigen in the specimen fluid.

In nephelometry, an antigen-antibody reaction is carried out in a gel or solution and the amount of an insoluble precipitate formed is measured. Even when the amount of an antigen in a specimen fluid to be tested is small and the amount of a precipitate formed is small, laser nephelometry wherein diffusion of laser is utilized can be suitably employed.

When employing these immunoassay methods in the determination method of the present invention, to set any special conditions, procedures and the like is not required. That is, the determination system of the protein, etc. of the present invention can be constructed based on conventional conditions and procedures in respective methods together with conventional artisan's technical consideration.

As for details of these general technical means, reference can be made to various reviews, texts and the like, for example, Hiroshi Irie, Ed., Radioimmunoassay, Kodan-sha (1974); Hiroshi Irie, Ed, Second Series, Radioimmunoassay, Kodan-sha (1979); Eizi Ishikawa et al., Ed., Enzyme Immunoassay, Igaku-shoin (1978); Eizi Ishikawa et al., Ed., Second Series, Enzyme Immunoassay, Igaku-shoin (1982); Eizi Ishikawa et al., Third Series, Enzyme Immunoassay, Igaku-shoin (1987); Method in Enzymology, Vol. 70, Immunochemical Techniques (Part A)), Academic Press; ibid., Vol. 73, Immunochemical Techniques (Part B); ibid., Vol. 74, Immunochemical Techniques (Part C); ibid., Vol. 84, Immunochemical Techniques (Part D: Selected Immunoassays); ibid., Vol. 92, Immunochemical Techniques (Part E: Monoclonal Antibodies and General Immunoassay Methods); ibid., Vol. 121, Immunochemical Techniques (Part I: Hybridoma Technology and Monoclonal Antibodies and the like.

As described hereinabove, the protein, etc. of the present invention can be determined at high sensitivity by using an antibody against the protein, etc. of the present invention.

In addition, the antibody of the present invention can be used for detecting the protein, etc. present in a specimen fluid such as a body fluid, tissue, etc. Further, the antibody can be used for preparation of an antibody column to be used for purification of the protein, etc. of the present invention, detection of the protein, etc. in each fraction obtained during purification thereof, analyzing behavior of the protein, etc. in cells to be tested, and the like.

(4) Screening for candidate compounds useful as drugs for various diseases

Like the protein, etc. of the present invention, compounds and their salts which promote the function of the protein, etc. of the present invention, for example, the above-described inhibitory function of transcription activity of a transcription factor (e.g., AP-1) can be used as drugs for prophylaxis and therapy of various diseases. Then, the protein, etc. of the present invention are useful as reagents for screening for such compounds and their salts which promote the function of the protein, etc. of the present invention.

That is, the present invention also provides:

(a) a method for screening for a compound which promote the function of the protein, etc. of the present invention (hereinafter sometimes referred to as a function promoting substance of the protein etc. of the present invention) which comprises using the protein, etc. of the present invention; more specifically, (b-1) a method for screening for a function promoting substance of the protein etc. of the present invention which comprises comparing a feature upon (i) cultivation of cells containing DNA encoding a transcription factor and DNA encoding the protein, etc. of the present invention and that upon (ii) cultivation of cells containing DNA encoding a transcription factor and DNA encoding the protein, etc., of the present invention in the presence of a compound to be tested; and (b-2) a method for screening for a function promoting substance of the protein etc. of the present invention which comprises comparing a feature upon (i) cultivation of cells containing a transcription factor and the protein, etc. of the present invention and that upon (ii) cultivation of cells containing a transcription factor and the protein, etc. of the present invention in the presence of a compound to be tested.

Specifically, the feature to be compared in the above screening methods (b-1) and (b-2) is, for example, inhibitory activity of a transcription factor by the protein, etc. of the present invention.

Examples of the transcription factor include a transcription factor which binds to a specific sequence of a DNA, a basal transcription factor which binds to about a promoter and the like. As a transcription factor which binds to a specific sequence of a DNA, for example, there are transcription factors belonging to Jun family (e.g., c-Jun, JunD, JunB, v-Jun), transcription factors belonging to Fos family (e.g., c-Fos, FosB, Fra1, Fra2, v-Fos), AP-1 (a complex of a transcription factor of Jun family and a transcription factor of Fos family), nuclear receptors (receptors for retinoic acid and various hydrophobic hormones), antioncogenic product (e.g., p53 protein), NF-κB, CREB, E2F, CTF and the like. As a basal transcription factor which binds to about a promoter, for example, there are TFIID (containing TATA box binding protein), TFIIH and the like. Among them, AP-1 and the like are preferred.

As the DNA encoding a transcription factor, for example, there may be mentioned known DNAs encoding the above-described transcription factors such as DNA encoding c-Jun (Proc. Natl. Acad. Sci. USA, 85, 9148–9152 (1988)), DNA encoding c-Fos (Proc. Natl. Acad. Sci. USA, 80, 3183–3187 (1983) and the like.

As the DNA encoding the protein, etc. of the present invention, the above-described DNA can be used.

As the cells, the above-described host cells can be used and cells having low AP-1 activity or cells without AP-1 activity, for example, mouse embryonic tumor cell F9 cell are suitable.

Introduction of the DNA encoding a transcription factor and the DNA encoding the protein, etc. of the present invention can be carried out according to the same manner as that described with respect to the above formation of the transformants. The cells containing a transcription factor and the protein, etc. of the present invention can be prepared by cultivation of the above-described cells containing the DNA encoding a transcription factor and the DNA encoding the protein, etc. of the present invention. Alternatively, naturally occurring cells containing a transcription factor and the protein, etc. of the present invention can also be used.

Examples of compounds to be tested include peptides, proteins, non-peptide compounds, synthetic compounds, fermentation products, cell extracts, plant extracts, animal tissue extracts and the like. They may be novel compounds or known compounds.

The "function" means, for example, that for inhibiting transcription activity of a transcription factor.

Indication for measuring transcription activity of a transcription factor is as follows.

(a) An amount of a related protein expressed by transcription activity of a transcription factor is measured.

The related protein is a protein whose transcription in a living body is originally regulated by a transcription factor and includes, for example, metallothionein (HMIIA), collagenases or the like.

For measurement of the amount of an expressed protein, for example, there are measurement of an amount of mRNA by Northern hybridization, measurement of an amount of protein by using an antibody, and the like. These measurements can be carried out according to per se known methods or their modifications.

When the expression level of a related protein is decreased by about 10% or more, preferably by about 20% or more, more preferably by about 50% or more upon addition of a test compound, the test compound can be selected as a compound which promotes function of an inhibitory factor of the transcription factor.

(b) A structural gene which can be used as an index is joined at the downstream from a transcription factor responsive promoter and an amount of the structural gene expressed is measured.

This is a method for measuring transcription activation capability of a transcription factor indirectly. That is, the amount of the expressed structural gene is measured, thereby utilizing activation of the transcription factor responsive promoter as an index.

As the transcription factor responsive promoter, for example, collagenase●TRE promoter which is AP-1 responsive promoter, or the like can be used.

As the structural gene to be used as the index, for example, a structural gene of an enzyme or the like can be used. Examples of the structural gene of the enzyme include luciferase structural gene, β-galactosidase structural gene, chloramphenicol acetyltransferase structural gene and the like.

Thus, by utilizing the structural gene of an enzyme, the expression level of the structural gene can be measured indirectly by the enzymatic activity of the enzyme expressed. The decrease in an amount of the enzyme expressed (i.e., the enzymatic activity) indicates the decrease in an amount of transcription from a transcription factor responsive promoter, i.e., inhibition of transcription activity of the transcription factor. Then, when the enzymatic activity is decreased by about 10% or more, preferably by about 20% or more, more preferably by about 50% or more upon addition of a test compound, the test compound can be selected as a compound which promotes the function of an inhibitory factor of a transcription factor. Specifically, this can be carried out according to the method described in Example 2 hereinafter.

Even when only a little activity of a transcription factor is inhibited, such inhibition is included in the activity to inhibit transcription activity of a transcription factors However, preferably, such activity is inhibition of transcription activity by about 10% or more, preferably by about 20% or more, more preferably by about 50% or more.

Promotion of function means, for example, such promotion that the inhibitory function of a transcription factor by the protein, etc. of the present invention in the above (ii) is increased by about 20% or more, preferably by about 50% or more, more preferably about 70% or more in comparison with that of the above (i).

As the cell culture broth, for example, phosphate buffer, Tris-HCl buffer or the like is used and the pH is adjusted to about 4 to about 10, preferably, about 6 to about 8.

When screening for test compounds is carried out according to the above method, a compound which promotes the inhibitory function of a transcription factor by the protein, etc. of the present invention in the above (ii) by about 20% or more, preferably by about 50% or more, more preferably about 70% or more in comparison with that of the above (i) can be selected as a compound which promotes the function of the protein, etc. of the present invention.

The kit for screening of the present invention comprises as an essential component the protein, etc. of the present invention. The protein, etc. of the present invention to be used for the kit may be the purified one. However, normally, it is preferred to use producer cells which can produce the protein, etc. of the present invention.

Examples of the kid for screening of the present invention include as follows.
(1) Reagents for screening
 (a) Producer cells
 Cells containing (i) DNA fragment having luciferase structural gene joined to the downstream of collagenase●TRE promoter which is AP-1 responsive promoter, (ii) DNA encoding the transcription factor c-Jun and (iii) DNA encoding the protein of the present invention (e.g., mouse embryonic tumor cell F9 cell) are cultivated by using DMEM medium containing 10% FBS (pH 7.0) in a 12-well plate at concentration of $10^4$ cells/well. Cultivation is carried out at 37° C. in 5% $CO_2$-95% air.
 (b) Cell washing buffer
 Dulbecco's phosphate-buffered saline (FBS).
 (c) Cytolytic solution
 25 mM glycylglycine (pH 7.8), 15 mM $MgSO_4$, 15 mM potassium phosphate buffer (pH 7.8), 4 mM ethylene glycol-O,O'-bis(2-aminoethyl)-N,N,N',N'-tetraacetic acid (EGTA) (pH 7.8), 1 mM dithiothreitol (DTT), and 1% Triton-X100.
 (d) Luminous substrate solution
 25 mM glycylglycine (pH 7.8), 15 mM $MgSO_4$, 15 mM potassium phosphate buffer (pH 7.8), 4 mM EGTA (pH 7.8), 1 mM DTT, 1 mM ATP (pH 7.5), 0.47 mM D-luciferin, and 0.27 mM coenzyme A.

(2) Measurement

A test compound is added to each plate and the producer cells of the above (1) (a) are cultivated at 37° C. for 24 hours. As a control, a group of the producer cells of the above (1) (a) which are cultivated at 37° C. for 24 hours without addition of the test compound is provided. After cultivation, the cells are washed twice with the above cell washing buffer. The above cytolytic solution is added thereto and the plate is maintained at room temperature for 10 minutes. The resultant cytolytic solution is transferred to a 1.5 ml plastic tube and centrifuged at 12,000 g at 4° C. for 5 minutes. The resultant supernatant (20 µl) is transferred to a 96-well plate and mixed with the above luminous substrate solution (100 µl). After 30 second, emission intensity at the wavelength of 562 nm is measured with AB-2100 Luminometer (ATTO).

When emission intensity is decreased by about 10% or more, preferably by about 20% or more, more preferably by about 50% or more by addition of a test compound, such test compound can be selected as a compound which promotes the function of the protein, etc. of the present invention.

The compounds or their salts obtained by the screening method or the screening kit of the present invention are selected from the above compounds to be tested, for example, peptides, proteins, non-peptide compounds, synthetic compounds, fermentation products, cell extracts, plant extracts, animal tissue extracts and the like, and they promote the function of the protein, etc. of the present invention.

The compounds which promote the function of the protein, etc. of the present invention include compounds which show inhibitory function of a transcription activity of a transcription factor (e.g., AP-1, etc.) by themselves to promote the function of the protein, etc. of the present invention arithmetically or synergistically, and compounds which do not show the inhibitory function by themselves but promote the function of the protein, etc. of the present invention.

In particular, preferably, the salts of the compounds are pharmaceutically acceptable acid addition salts. Examples of such salts include salts with the above-described inorganic and organic acids and the like.

Like the above-described protein, its partial peptide or their salts of the present invention, the compounds or their salts which promote the function of the protein, etc. of the present invention are useful as safe and low toxic prophylactic or therapeutic drugs of various diseases.

When the compound or its salt obtained by the screening method or the screening kit of the present invention is used for a prophylactic or therapeutic drug-as described above, like the above-described protein, its partial peptide or their salts of the present invention, any conventional manner can be employed.

Since the pharmaceutical composition thus obtained is safe and low toxic, it can be administer to a human being and other mammals.

Although the amount of the compound or its salt of the present invention to be administered is varied according to particular diseases, in general, for oral administration to an adult human tumor patient (as 60 kg body weight), it is administered in an amount of about 1 mg/day to about 500 mg/day. For parenteral administration to an adult human being (as 60 kg body weight), for example, in the form of an injectable preparation, it can be administered in an amount of about 0.1 mg/day to about 500 mg/day intravenously, though the single dosage is varied according to particular diseases, routes of administration, etc. As for other animals, it can be administered in the above amount with converting it into that for the body weight of 60 kg.

Moreover, the protein, its partial peptide or their salts of the present invention have function of a cell cycle control factor. Therefore, if a compound which inhibits the function as a cell cycle control factor of the protein, etc. of the present invention (i.e., cell cycle inhibitor) can be screened, such a compound is useful for developing medicine, for example, a prophylactic or therapeutic drug of various diseases, for example, tumors (e.g., cancer such as bladder carinoma, breast cancer, cancer of uterine carvix, cancer of large intestine (carcinoma of colon and rectum), lung cancer, non-small cell lung cancer, ovarian cancer, prostatic cancer, small cell lung cancer, gastric cancer, etc., chronic lymphocytic leukemia, chronic myelogenous leukemia, malignant melanoma, metastasis, multiple myeloma, non-Hodgkin lymphoma, etc.), acute bacterial periostitis, acute myocardial infarction, acute pancreatitis, acute viral encephalitis, adult respiratory distress syndrome, rigid spondylitis, bacterial pneumonia, chronic pancreatitis, gastritis, hepatitis A, hepatitis B, hepatitis C, herpes simplex infection, varcellazoater virus infection, Hodgkin disease, AIDS infection, human papillomavirus infection, influenza virus infection, active staphylococcal infection, osteoarthritis, bone atropy (prophylaxis of osteoporosis), osteoporosis, bone Behcet disease, pain, peptic ulcer, peripheral vessel disease, rheumatoid arthritis, septic shock, systemic mycosis, valvular disease of heart and the like. Thus, the protein, etc. of the present invention is also useful as a relent for screening for a cell cycle inhibitor.

The screening of a cell cycle inhibitor can be carried out by a per se known method or Its modification.

In the specification and drawings, the abbreviations of bases, amino acids and the like are those according to IUPAC-IUB Commission on Biochemical Nomenclature or those conventionally used in the art. The examples are as follows.

When the amino acid has an optical isomer, the amino acid is L-isomer unless otherwise stated.

DNA: deoxyribonucleic acid cDNA: complementary deoxyribonucleic acid

A: adenine

T: thymine

G: guanine

C: cytosine

RNA: ribonucleic acid mRNA: messenger ribonucleic acid dATP: deoxyadenosine triphosphate dTTP: deoxythymidine triphosphate dGTP: deoxyguanosine triphosphate dCTP: deoxycytidine triphosphate ATP: adenosine triphosphate EDTA: ethylenediaminetetraacetic acid SDS: sodium dodecylsulfate Gly: glycine Ala: alanine Val: valine Leu: leucine Ile: isoleucine Ser: serine Thr: threonine Cys: cysteine Met: methionine Glu: glutamic acid Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
Me: methyl group
Et: ethyl group
Bu: butyl group
Ph: phenyl group
TC: thiazolidin-4(R)-carboxamide group The substituents, protecting groups and reagents often used herein are shown by the following abbreviations.
Tos: p-toluenesulfonyl
CHO: formyl
Bzl: benzyl
Cl$_2$Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluoroenylmethoxycarbonyl
HoBt: 1-hydroxybenztriazole
HOOBt: 3,4-dihydro-3-hydroxy-4-oxo-1,2,3-benzotriazine
HONB: 1-hydroxy-5-norbornen-2,3-dicarboxyimide
DCC: N,N'-dicylcohexylcarbodiimide The sequences in the Sequence Listing of the present specification are as follows.

SEQ ID NO:1
This sequence represents an amino acid sequence of the protein of the present invention.

SEQ ID NO:2
This sequence represents a nucleotide sequence of DNA encoding the protein of the present invention which has the amino acid sequence of SEQ ID NO:1.

SEQ ID NO:3
This sequence represents a nucleotide sequence of a primer used for cloning of DNA encoding the protein of the present invention in Example 1 hereinafter.

SEQ ID NO:4
This sequence represents a nucleotide sequence of a primer used for cloning of DNA encoding the protein of the present invention in Example 1 hereinafter.

SEQ ID NO:5
This sequence represents a nucleotide sequence of a primer used for cloning of DNA encoding the protein of the present invention in Example 3 hereinafter.

SEQ ID NO:6
This sequence represents a nucleotide sequence of a primer used for cloning of DNA encoding the protein of the present invention in Example 3 hereinafter.

SEQ ID NO:7
This sequence represents an amino acid sequence of a peptide corresponding to the 1024th amino acid to the 1043rd amino acid of the protein represented by SEQ ID NO:1.

The transformant Escherichia coli DH5α/pBHC1 obtained in Example 1 hereinafter has been deposited with National Institute of Bioscience and Human-Technology (NIBH), Agency of Industrial Science & Technology Ministry of International Trade & Industry (1–3, Higasi 1-chome, Tsukubashi Ibaraki, 305 Japan) according to the Budapest Treaty under the accession number of FERN BP-5755 since Nov. 22, 1996 and also deposited with Institute for Fermentation Osaka (IFO, 17–85, Juso-honmachi 2-chome Yodogawa-ku, Osaka, 532 Japan) under accession number of IFO 16045 since Nov. 21, 1996. The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

The following examples further illustrate the present invention in detail but are not to be construed to limit the scope thereof. Gene manipulation was carried out according to the method described in molecular Cloning, 2nd Edition (1989).

EXAMPLE 1

Cloning of cDNA Encoding an Inhibitory Factor of a Human Transcription Factor

The whole RNAs in cell were extracted from human myelocytic leukemia cell strain X562 cell by guanidine isothiocyanate method and cDNA was synthesized by Time-saver cDNA synthesis kit (Pharmacia Biotech) using Oligo (dT)12–18 (Pharmacia Biotech) as a primer. The cDNA was used as a template of PCR (polymerase chain reaction). In addition, for PCR primers, two synthetic primers (SEQ ID: NO 3 and SEQ ID: NO 4) were prepared by Expedite Nucleic Acid Synthesis System 8909 (Nippon Perceptive). PCR was carried out by preparing a mixture of 1 µg of template cDNA, each 40 pmol of the above primers, each 10 nmol of dATP, dCTP, dGTP and dTTP (Takara Shuzo), 2.6 units of Expand™ High Fidelity PCR system enzyme mix (Boehringer Mannheim) and 5 µl of Expand™ High Fidelity PCR system 10× buffer with MgCl$_2$ and bringing it to the final volume of 50 µl. PCR was carried out using Gene-Amp™ PCR system 2400 (Perkin Elmer). The temperature cycle program was first 2 minutes at 94° C.; then 15 seconds at 94° C., 30 seconds at 55° C. and 4 minutes at 68° C., for 10 cycles; and, finally, 15 seconds at 94° C., 30 seconds at 60° C. and (4+⅓×N) minutes at 68° C. (wherein N is the number of cycle, i.e., 1 to 25), for 25 cycles.

A single band of 4.1 kb was identified as the PCR product by agarose gel electrophoresis and the cDNA fragment was extracted and recovered. Then, terminal modification was carried out with T4 DNA polymerase (Takara Shuzo) and T4 polynucleotide kinase (Takara Shuzo) and the fragment was jointed to SmaI restriction site of the phagemide vector pBluescript™ II SK(–) (Stratagene) by using T4 DNA ligase (Takara Shuzo). Escherichia coli DH5α strain was transformed with it and the transformant, Escherichia coli DH5α/pBHC1 having the plasmid pBHC1 into which the cDNA fragment was inserted, was obtained from the resultant ampicillin resistant (50 µg/ml) colonies.

The nucleotide sequence of the inserted cDNA fragment was determined as follows. 12 subclone plasmids were constructed from the plasmid by further fragmenting the cDNA fragment inserted therein. For each of the plasmids, a reaction mixture was prepared by Thermo Sequenase™ fluorescent labeled primer cycle sequencing kit with 7-deaza-dGTP (Amersham) using IRD Infrared Dye Labeled Primer M13 Forward (−38) or IRD Infrared Dye Labeled Priomer M13 Reverse (Aloka) as a primer and the reaction was carried out with GeneAmp™ PCR system 2400. The electrophoresis and sequencing of the reaction product were carried out by using LI-COR™ DNA sequencer 4000L (Aloka). The nucleotide sequences of each subclone DNA were combined to determined the nucleotide sequence of the cDNA fragment inserted into pBHC1.

As a result, the cDNA had the nucleotide sequence of 4088 bases as shown by FIGS. 1A, 1B, 1C, 1D, 1E and 1F and encoded the novel protein having 1071 amino acids represented by SEQ ID NO:1. As for this protein, no homology to known proteins of higher organisms including a human being was observed by comparison of homology on a level of amino acids according to Clustal method. And, in comparison with any known protein, only 51.6% of homology to *Schizosacchromyces pombe* crm1$^+$ and only 45.8% of homology to *Saccharomyces cerevisiae* CRM1 were observed.

EXAMPLE 2

Screening for Compounds Which Promote Function of an Inhibitory Factor of a Transcription Factor of the Present Invention A DNA fragment wherein the AP-1 responsive promoter, collagenase●TRE promoter (TRE col) (The Journal of Biological Chemistry, 266, 16485–16490 (1991), is joined at the downstream of luciferase structural gene and a plasmid having neomycin resistance gene (e.g., a plasmid obtained by replacing MMTV LTR promoter region of pMAMneo-LUC (Clontech) with collagenase●TRE promoter, etc.) are constructed. They are introduced into mouse embryonic tumor cell F9 and a neomycin resistant strain is selected to obtain F9 (Neo)/TRE col-LUC transformant.

On the other hand, a plasmid pCMV-c-jun wherein cDNA encoding c-Jun, which is one of AP-1 constituent proteins and has high transcription activation capability (Proc. Natl. Acad. Sci. USA, 85, 9148–9152 (1988), is joined at the downstream of CMV promoter region of a plasmid having that promoter (e.g., pRc/CMV, pcDNA3, etc., Invitrogen) and a plasmid pCMV-hCRM1 wherein the cDNA encoding the protein of the present invention as prepared in Example 1 is joined at the downstream of CMV promoter region of a plasmid having that promoter are constructed.

F9(Neo)/TREcol-LUC transformant is cultivated on a 12-well plate and (a) the plasmid pCMV-c-jun and (b) both plasmids pCMV-c-jun and pCMV-hCRM1 are introduced into cells by a lipofection method to prepare (a) F9 (Neo)/TRE col-LUC transformant having the plasmid pCMV-c-jun and (b) F9 (Neo)/TRE col-LUC transformant having the plasmids pCMV-c-jun and pCMV-hCRM1, respectively.

Then, a compound to be tested is added to each well containing F9 (Neo)/TRE col-LUC transformant having the plasmids pCMV-c-jun and pCMV-hCRM1 of the above (b) and cultivated at 37° C. for 24 hours. As a control, F9 (Neo)/TRE col-LUC transformant having the plasmids pCMV-c-jun and pCMV-hCRM1 of the above (b) is cultivated at 37° C. for 24 hours without addition of the compound to be tested. In addition, F9 (Neo)/TRE col-LUC transformant having the plasmid pCMV-c-Jun of the above (a) is also cultivated at 37° C. for 24 hours.

After cultivation, cells are washed twice with Dulbecco's phosphate-buffered saline (FBS). A cytolytic solution (25 mM glycylglycine (pH 7.8), 15 mM MgSO$_4$, 15 mM potassium phosphate buffer (pH 7.8), 4 mM EGTA (pH 7.8), 1 mM dithiothreitol. (DTT), and 1% Triton-X100) is added and the mixture is maintained at room temperature for 10 minutes. The resultant cytolytic solution is transferred to a 1.5 ml plastic tube and centrifuged at 12,000 g at 4° C. for 5 minutes. The resultant supernatant is transferred to a 96-well plate and mixed with a luminous substrate solution (25 mM glycylglycine (pH 7.8), 15 mM MgSO$_4$, 15 mM potassium phosphate buffer (pH 7.8), 4 mM EGTA (pH 7.8), 1 mM DTT, 1 mM ATP (pH 7.5), 0.47 mM D-luciferin, and 0.27 mM coenzyme A). After 30 second, emission intensity at the wavelength of 562 nm is measured with AB-2100 Luminometer (ATTO).

First, the decrease in emission intensity of the culture group of F9 (Neo)/TRE col-LUC transformant having the plasmids pCMV-c-jun and pCMV-hCRM1 of the above (b) in comparison of that of the culture group of F9 (Neo)/TRE col-LUC transformant having the plasmid pCMV-c-jun of the above. (a) is confirmed.

Then, when emission intensity of the group of F9 (Neo)/TRE col-LUC transformant having the plasmids pCMV-c-jun and pCMV-hCRM1 of the above (b) cultivated in the presence of a test compound is decreased in comparison of that cultivated in the absence of the test compound, such test compound can be selected as a compound which promotes the function of the inhibitory factor of a transcription factor of the present invention.

EXAMPLE 3

Complementation to Fission Yeast crm1 Mutation With cDNA Encoding the Protein of the Present Invention PCR was carried out in a reaction system using the plasmid, pBHC1, obtained in Example 1 as a template, two synthetic oligonucleotides represented by SEQ ID NO:5 and SEQ ID NO:6 of the Sequence Listing as primers, and Expand™ High Fidelity PCR system enzyme mix (Boehringer Mannheim) as a DNA polymerase.

A reaction mixture was prepared by mixing 0.1 µg of pBHC1, each 40 pmol of the above primers, each 10 nmol of dATP, dCTP, dGTP and dTTP (Takara Shuzo), 2.6 units of Expand™ High Fidelity PCR system enzyme mix and 5 µl of Expand™ High Fidelity PCR system 10× buffer with MgCl$_2$ and bringing it to the final volume of 50 µl. Gene-Amp™ PCR system 2400 thermal cycler (Perkin Elmer Applied Biosystems) was used. The temperature cycle program was 2 minutes at 94° C., 15 seconds at 94° C., 30 seconds at 60° C. and 1 minute at 72° C. for 20 cycles. After completion of the reaction, the reaction mixture was subjected to 1.0% agarose gel electrophoresis to identify a band corresponding to a single DNA fragment amplified by the PCR. Then, the DNA fragment was recovered and purified by GENECLEAN III kit (Bio 101). The purified DNA was further digested with the restriction enzyme, BamHI, and subjected to 1.0% agarose gel electrophoresis, again, followed by recovering and purifying it. The resultant DNA fragment was inserted into and joined to BamHI cloning site of the known plasmid vector, pDB248' (Molecular and General Genetics, 187, 326–329 (1982)), with T4 DNA ligase (Takara Shuzo). The reaction mixture was introduced into *Escherichia coli* DH5α and cultivated on LB agar medium containing ampicillin. Among ampicillin resistant transformant colonies grown, one clone was selected and plasmid DNA prepared therefrom was named as pDHC1.

On the other hand, the purified DNA obtained after completion of the above PCR was digested with the restriction enzymes, NdeI and BamHI, and subjected to 1.0% agarose gel electrophoresis, again, followed by recovering and purifying it. The resultant DNA fragment was inserted into and joined to NdeI/BamHI cloning site of the known plasmid vector, pREP1 (Gene, 123, 131–136 (1993)), with T4 DNA ligase (Takara Shuzo). The reaction mixture was introduced into *Escherichia coli* DH5α and cultivated on LB agar medium containing ampicillin. Among ampicillin resistant transformant colonies grown, one clone was selected and plasmid DNA prepared therefrom was named as pR1HC1.

The fission yeast, *S. pombe*, was transformed by per se known lithium acetate method (Experiments with Fission Yeast: a Laboratory Course Manual, Cold Spring Harbor Laboratory Press, Cold Spring Harbor, N.Y., 1993).

The above pDHC1 was introduced into *S. pombe* AC1 strain (h⁻leu1-32 crm1-809) (Journal of Cell Biology, 108, 1195–1207 (1989)), and the above pR1HC1 was introduced into *S. pombe* JY266 strain (h⁺leu1-32) (The Journal of Biological Chemistry, 269(9), 6320–6324 (1994)), respectively. As a result, although, normally, AC1 strain could not grow on YPD agar medium (1% yeast extract, 2% polypeptone, 2% glucose and 2% agar) at 18° C. because of its cold sensitive mutation (crm1-809) (Journal of Cell Biology, 108, 1195–1207 (1989)), pDHC1-introduced AC1 strain could grow on the medium. On the other hand, although pR1HC1-introduced JY266 strain could grow on a yeast minimal agar medium (Experiments with Fission Yeast: a Laboratory Course Manual, Cold Spring Harbor Laboratory Press, Cold Spring Harbor, N.Y. (1993)) in the presence of 10 mg/ml of thiamin, it could not grow on the yeast minimal agar medium in the absence of thiamin wherein nmt1 promoter activity was introduced.

In view of the above, it has been clarified that DNA encoding the protein of the present invention complements to fission yeast crm1 mutation and that excess expression of the gene inhibits the growth of fission yeast cells.

The results of the above experiment are shown in Table 1.

TABLE 1

| Host | AC1 | AC1 | JY266 | JY266 | JY266 |
|---|---|---|---|---|---|
| Plasmid introduced | pDB248' | pDHC1 | pR1HCl | pR1HCl | pREP1 |
| Medium | YPD | YPD | minimal + thiamin | minimal − thiamin | minimal − thiamin |
| Growth temp (°C.) | 18 | 18 | 30 | 30 | 30 |
| Growth* capability | − | − | + | − | + |

Note: − no growth, + growth

EXAMPLE 4

Preparation of Anti-CRM1 Antiserum and Western Blotting Analysis of HeLa Cell Whole Proteins Using the Serum Anti-CRM1 antiserum was prepared as follows.

A peptide represented by SEQ ID NO:7 corresponding the 1024th amino acid and the 1043rd amino acid of the protein of the present invention shown in SEQ ID NO:1 was synthesized chemically by a known method. The peptide was coupled to KLH (keyhole limpet hemocyanin) and it was injected subcutaneously in the back of rabbit in an amount corresponding to 1 mg of the antigen peptide together with Freund's Complete Adjuvant (FCA) to provide a primary immunization. After two weeks, as a secondary immunization, the peptide was injected subcutaneously in the back and intramuscularly in the thigh in an amount corresponding to 1 mg of the antigen peptide together with Freund's Incomplete Adjuvant (FIA). Then, according to the same manner as the secondary immunization, immunization was repeated four times every third week. In the eleventh week, whole blood was collected, the serum was fractionated by a known method to obtain anti CRM1 antiserum.

HeLa cells were cultivated in Dulbecco modified Eagle's medium containing 10% bovine serum and suspended in a cytolytic buffer (0.5% SDS, 0.05M Tris-HCl (pH 8.0), 1 mM dithiothreitol). The suspension was maintained in boiling water for 5 minutes and centrifuged at 15,000 rpm at 4° C. for 90 minutes to separate a supernatant as a HeLa cell whole protein extract. The proteins were subjected to 10% polyacrylamide gel electrophoresis. After electrophoresis, the migrated proteins were transferred on a polyvinylidene difluoride (PVDF) membrane (Millipore) in 25 mM Tris-192 mM Glycine-20% methanol buffer (pH 8.3) with a protein blotting apparatus (Biorad). The membrane was maintained in TBST buffer (10 mM Tris-HCl (pH 8.0), 150 mM NaCl, 0.05% Tween 20) supplemented with 5% skim milk and containing 50-fold diluted anti-CRM1 antiserum at room temperature for 1 hour and then 4° C. for 8 hours. After washing with TBST buffer, the membrane is maintained in TBST buffer supplemented with 5% skim milk and containing 1,000-fold diluted anti-rabbit IgG, horse radish peroxidase linked whole antibody from donkey (Amersham) at room temperature for 1 hour and then washed again with TBST buffer. Then, a chemical emission reaction was carried out using ECL Western blotting detection reagents (Amersham) and the PVDF membrane was contacted with a X-ray film, followed by exposure and development of the film.

As a result, as shown in FIG. 2, a signal at the position of the molecular weight of 110 kDa which was deduced from the amino acid sequence of the protein of the present invention was detected.

As described hereinabove, the protein, its partial peptide or their salts of the present invention can inhibit transcription activity of a transcription factor, for example, a tumor-related transcription factor such as AP-1, etc. Therefore, the protein, its partial peptide or their salts of the present invention, and DNA encoding the protein or its partial peptide of the present invention are useful as medicine such as prophylactic and therapeutic drugs of, for example, tumors. In addition, DNA encoding the protein or its partial peptide of the present invention is useful as a gene diagnosing drug because it can detect abnormality of expression of the DNA.

The antibody against the protein, its partial peptide or their salts of the present invention can specifically recognize the protein, its partial peptide or their salts of the present invention. Therefore, it can be used for quantitative determination of the protein, etc. of the present invention in a specimen fluid, purification of the protein, etc. of the present invention, analysis of behavior of the protein, etc. of the present invention in cells to be tested and the like.

Furthermore, the protein, its partial peptide or their salts of the present invention is useful as a reagent for screening for compounds or their salts which promote the function of the protein, its partial peptide or their salts of the present invention.

What is claimed is:

1. An isolated polypeptide which comprises the amino acid sequence set forth as SEQ ID NO:1 or its salt.

2. A composition comprising the polypeptide of claim 1 or a salt thereof and a carrier or diluent.

3. A kit for screening for compounds which promote the function of the polypeptide of claim 1 or a salt thereof which comprises the polypeptide of claim 1 or a salt thereof.

4. An isolated polypeptide comprising the amino acid sequence set forth as SEQ ID NO:7.

5. An isolated polypeptide comprising at least 50 contiguous amino acids of the amino acid sequence set forth as SEQ ID NO:1.

6. The isolated polypeptide of claim 5 comprising at least 100 contiguous amino acids of the amino acid sequence set forth as SEQ ID NO:1.

7. The isolated polypeptide of claim 5 comprising amino acids 86 to 940 of the amino acid sequence set forth as SEQ ID NO:1.

* * * * *